US009611258B2

(12) United States Patent
Ross et al.

(10) Patent No.: US 9,611,258 B2
(45) Date of Patent: Apr. 4, 2017

(54) DUAL MEK/PI3K INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Brian D. Ross, Ann Arbor, MI (US); Marcian Van Dort, Ann Arbor, MI (US); Christopher Whitehead, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/771,233

(22) PCT Filed: Mar. 12, 2014

(86) PCT No.: PCT/US2014/023860
§ 371 (c)(1),
(2) Date: Aug. 28, 2015

(87) PCT Pub. No.: WO2014/164942
PCT Pub. Date: Oct. 9, 2014

(65) Prior Publication Data
US 2016/0002212 A1   Jan. 7, 2016

Related U.S. Application Data

(60) Provisional application No. 61/779,462, filed on Mar. 13, 2013.

(51) Int. Cl.
C07D 405/14 (2006.01)
C07D 403/04 (2006.01)

(52) U.S. Cl.
CPC ......... C07D 405/14 (2013.01); C07D 403/04 (2013.01)

(58) Field of Classification Search
CPC ..................... C07D 405/14; C07D 403/04
See application file for complete search history.

(56) References Cited

U.S. PATENT DOCUMENTS

| 7,897,792 | B2 | 3/2011 | Iikura et al. |
| 2010/0249099 | A1 | 9/2010 | Rewcastle et al. |
| 2011/0009398 | A1 | 1/2011 | Sakai et al. |
| 2011/0009405 | A1 | 1/2011 | Rewcastle et al. |
| 2011/0053907 | A1 | 3/2011 | Rewcastle et al. |
| 2011/0092700 | A1 | 4/2011 | Iikura et al. |
| 2011/0166191 | A1 | 7/2011 | Zhang et al. |
| 2013/0040912 | A1 | 2/2013 | Cmiljanovic et al. |

FOREIGN PATENT DOCUMENTS

WO   WO-02/06213 A2   1/2002

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Al-Lazikani, B., et al., Combinatorial Drug Therapy for Cancer in the Post-Genomic Era, *Nature Biotechnology*, 2012, vol. 30, No. 7, pp. 679-692.
Apsel, Beth, et al., "Targeted Polypharmacology: Discovery of Dual Inhibitors of Tyrosine and Phosphoinositide Kinases," *Nature Chemical Biology*, 2008, vol. 4, No. 11, pp. 691-699.
Atefi, M., et al., "Reversing Melanoma Cross-Resistance to BRAF and MEK Inhibitors by Co-Targeting the AKT/mTOR Pathway," *PLoS one*, 2011, vol. 6, No. 12, p. e28973.
Engelman, J. A., et al., "Effective Use of PI3K and MEK Inhibitors to Treat Mutant Kras G12D and PIK3CA H1047R Murine Lung Cancers," *Nature Medicine*, 2008, vol. 14, No. 12, pp. 1351-1356.
Kaiser, J., "Combining Targeted Drugs to Stop Resistant Tumors," *Science*, 2011, vol. 331, No. 6024, pp. 1542-1545.
Park, H., "Discovery of MEK/PI3K Dual Inhibitor Via Structure-Based Virtual Screening," *Bioorganic & Medicinal Chemistry Letters*, 2012, vol. 22, No. 15, pp. 4946-4950.
Rewcastle, G. W., et al., "Synthesis and Biological Evaluation of Novel Analogues of the Pan Class I Phosphatidylinositol 3-Kinase (PI3K) Inhibitor 2-(Difluoromethyl)-1-[4,6-di(4-Morpholinyl)-1,3,5-Triazin-2-yl]-1H-Benzimidazole (ZSTK474)," *Journal of Medicinal Chemistry*, 2011, vol. 54, No. 20, pp. 7105-7126.
Roberts, P. J., "Combined PI3K/mTOR and MEK Inhibition Provides Broad Antitumor Activity in Faithful Murine Cancer Models," *Clinical Cancer Research*, 2012, vol. 18, No. 19, pp. 5290-5303.
International Search Report in International Patent Application No. PCT/US2014/023860, dated Jul. 7, 2014.
Park et al., Discovery of MEK/PI3K dual inhibitor via structure-based virtual screening, Bioorg. Med. Chem. Lett., 22(15):4946-50 (2012).
Supplementary European Search Report, European patent application No. EP14779150, mailed Jul. 20, 2016.

* cited by examiner

Primary Examiner — Shawquia Jackson
(74) Attorney, Agent, or Firm — Marshall, Gerstein & Borun LLP

(57) ABSTRACT

Dual inhibitors of MEK and PI3K and compositions containing the same are disclosed. Methods of using the dual MEK/PI3K inhibitors in the treatment of diseases and conditions wherein inhibition of MEK and PI3K provides a benefit, like cancers, also are disclosed.

20 Claims, No Drawings

DUAL MEK/PI3K INHIBITORS AND THERAPEUTIC METHODS USING THE SAME

CROSS-REFERENCE TO RELATED APPLICATION

This is the U.S. national phase of PCT/US2014/023860, filed Mar. 12, 2014, which claims the benefit of U.S. Provisional Patent Application No. 62/779,462, filed Mar. 13, 2013, incorporated herein by reference in its entirety.

FIELD OF THE INVENTION

The present invention relates to difunctional inhibitors of MEK and PI3K and to therapeutic methods of treating conditions and diseases wherein inhibition of MEK and PI3K provides a benefit. The present dual MEK/PI3K inhibitors are useful as agents for cancer therapy, either alone or in combination with radiation and/or other chemotherapeutics.

BACKGROUND OF THE INVENTION

Aberrant hyperactivation of KRAS plays a prominent role in tumor initiation and progression in a broad spectrum of human cancers. KRAS mutations comprise 86% of all RAS mutations and are associated with the highest frequency, roughly 22%, of all human malignancies (1). The incidence of KRAS mutations is especially high in pancreatic and colorectal malignancies, where it occurs at a frequency of greater than 90 and greater than 40%, respectively. Pancreatic and colorectal cancers are among the most lethal of all cancers and are the fourth and third leading cause of cancer deaths in the US (2). Approximately 80% of all pancreatic cancer cases present with locally advanced or metastatic disease, which precludes surgical intervention. Currently, there are no curative options for the treatment of KRAS-activated cancers. Treatment options for KRAS mutant patients with metastatic colorectal cancer who have failed first-line chemotherapy with a fluoropyrimidine and oxaliplatin are also limited.

Efforts to develop drugs that directly target mutant KRAS remain challenging because specificity issues are problematic. Consequently, efforts at pharmacologic intervention of KRAS signaling have focused intensively in recent years on downstream targets in the two central RAS effector pathways, RAF/MEK/ERK and PI3K/AKT/mTOR (3, 4). RAF and MEK have spawned a number of drug discovery programs that have resulted in attractive clinical candidates (5-7). Clinical activity of BRAF inhibitors likely will be restricted to patients with BRAF mutated tumors because the absence of a BRAF mutation is associated with induction, rather than inhibition, of MAPK signaling in response to this targeted approach (8-10). In contrast, MEK inhibitors have been shown to exert antiproliferative effects in roughly half of the KRAS mutant tumors tested (11). It is encouraging that the MEK inhibitor CI-1040, as well as trametinib, have both elicited objective responses in Phase 1 testing (12, 13). MEK inhibition therefore is a viable approach for the treatment of KRAS activated cancers, but in a monotherapy setting, MEK inhibition is unlikely to produce the degree of activity needed to significantly impact outcome in this refractory patient population.

One strategy to improve upon MEK inhibitor single agent activity is the additional targeting of PI3K signaling. This combination strategy is based on in vitro and in vivo evidence suggesting that KRAS mutant tumors require dual inhibition of both the MAPK and PI3K pathways to achieve maximal inhibition of tumor growth (11, 14-16). Release of negative feedback loops has been shown to lead to activation of the alternate pathway when either one is inhibited (16, 17). Activation of the PI3K pathway, commonly due to PI3KCA mutations or PTEN loss, represents a major resistance mechanism to MEK inhibitor therapy in KRAS mutant cancers. Combined inhibition of both pathways leads to a significant increase in apoptosis and tumor shrinkage (18).

Because the RAS/RAF/MEK/ERK signal transduction pathway is activated in a significant percentage of the most aggressive and deadly forms of human cancers, several small molecule inhibitors targeting this pathway have either been FDA approved or are in active clinical development. Unfortunately, despite the clinical efficacy of a commercially-available BRAF inhibitor, i.e., PLX4032 or Vemurafenib, in treating tumors bearing both BRAF and KRAS activating mutations, the drug is ineffective against tumors with native BRAF due to paradoxical induction of ERK signaling.

MEK and PI3K inhibitors therefore are known in the art. For example, Iikura et al. U.S. Pat. No. 7,897,792 discloses a class of coumarin-based MEK inhibitors. PI3K inhibitors are disclosed, for example, in U.S. Patent Nos. 2010/0249099; 2011/0009405; and 2011/0053907. The combined use of PI3K and MEK inhibitors to treat lung cancer is disclosed, for example, in Engelman et al., Nature Medicine, Vol. 14, Number 14, pages 1351-56 (2008).

However, a need still exists in the art for compounds and methods to treat cancers and other diseases and conditions by inhibition of MEK and PI3K. Despite the discovery of small molecular inhibitors MEK and PI3K, the design of potent, inhibitors of MEK and PI3K remains a significant challenge in modern drug discovery. Accordingly, a need still exists in the art for MEK and PI3K inhibitors having physical and pharmacological properties that permit use of the inhibitors in therapeutic applications. The present invention provides bifunctional compounds designed to bind to MEK and PI3K, and to inhibit MEK and PI3K activity.

SUMMARY OF THE INVENTION

The present invention is directed to a single compound that co-targets the MAP kinase and PI3K pathways, and to methods of treating a cancer by administering such a compound to an individual in need thereof. More particularly, the present invention is directed to novel bifunctional compounds that are capable of inhibiting two key signal transduction pathways (i.e., MEK, PI3K) implicated in tumor growth, progression, and metastasis. Individual PI3K and MEK inhibitors, chemically modified to accommodate linkers while maintaining high binding affinity towards their respective enzyme targets, are conjugated to provide the present bifunctional MEK/PI3K inhibitors. The present compositions inhibit KRAS-driven tumor progression by simultaneously targeting two critical regulatory nodes, MEK and PI3K, and in so doing intercept the cross-talk that occurs between their respective pathways.

The present invention therefore is directed to dual inhibitors of MEK and PI3K enzymes, to compositions comprising the inhibitors, and to methods of using the inhibitors in a therapeutic treatment of conditions and diseases wherein inhibition of MEK and PI3K activity provides a benefit. The present compounds are potent inhibitors of both MEK activator and PI3K activation, and are useful in the treatment of cancers, and particularly KRAS mutant tumors.

The present invention is directed to compounds having the following structural formula (I):

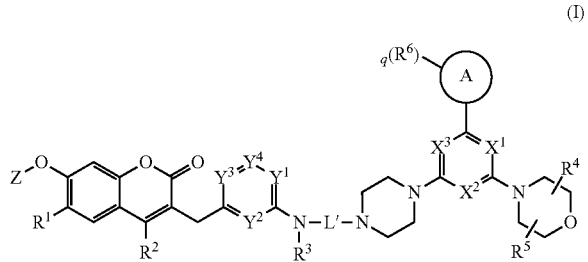

wherein Z is a heteroaryl group or $R^aR^bNCO$—;
$Y^1$ and $Y^2$, independently, are N or $CR^c$;
$Y^3$ and $Y^4$, same or different, are each $CR^d$;
$X^1$, $X^2$, and $X^3$, independently, are N or $CR^3$, wherein at least one of $X^1$, $X^2$, and $X^3$ is N;
A is cycloalkyl, heterocycyl, aryl, or heteroaryl;
L' is $J\text{-}(CH_2)_n\text{-}K$, wherein n is an integer 3, 4, 5, 6, 7, 8, or 9, $J\text{-}(CH_2)_m\text{-}N(R^7)\text{-}(CH_2)_p\text{-}K$, wherein m and p, independently, are integers 0, 1, 2, 3, 4, 5, or 6, and $R^7$ is H, methyl, ethyl, propyl or butyl,
$(CH_2O)_l$, $(CH_2CH_2O)_l$, wherein l is 5, 6, 7, 8, or 9, or —$(NHCHRC(=O))_q$—, wherein R, independently, is an amino acid residue, and q is an integer 3, 4, 5, 6, 7, 8, or 9;
J and K, independently, are (—C(=O)—, —C(=O)N—, —$SO_2$—, or —$CH_2$—;
$R^1$ is hydrogen, a halo, cyano, $C_{1-6}$alkyl, $C_{2-7}$alkenyl, carbamoyl, or $C_{2-7}$ alkynyl optionally substituted with a $C_{1-4}$acyl group;
$R^2$ is $C_{1-6}$alkyl optionally substituted with halo, OH, $C_{1-6}C(=O)R^a$, or $CH_2OC_{1-6}$ alkyl;
$R^3$ is hydrogen or $C_{1-6}$alkyl;
$R^4$ and $R^5$, independently are hydrogen or $C_{1-6}$alkyl, or $R^4$ and $R^5$ are taken together with the carbon to which they are bound to form $C_{1-6}$alkylene, $C_{1-6}$heteroalkylene, $C_{2-6}$alkenylene, or $C_{2-6}$heteroalkenylene;
$R^6$, independently, is cyano, halo, nitro, $C_{1-6}$alkyl, halo$C_{1-6}$ alkyl, $C_{2-6}$alkenyl, $C_{2-6}$alkynyl, $C_{3-7}$cycloalkyl, $C_{6-14}$aryl, $C_{7-15}$aralkyl, heteroaryl, heterocyclyl, —$C(O)R^e$, —$C(O)OR^e$, —$C(O)N(R^e)_2$, —$C(NR^e)N(R^e)_2$, —$OR^e$, —$OC(O)R^e$, —$OC(O)OR^e$, —$OC(O)N(R^e)_2$, —$OC(=NR^e)N(R^e)_2$, —$OS(O)R^e$, —$OS(O)_2R^e$, —$OS(O)N(R^e)_2$, —$OS(O)_2N(R^e)_2$, —$N(R^e)_2$, —$NR^eC(O)R^e$, —$NR^eC(O)N(R^e)_2$, —$NR^eC(=NR^e)N(R^e)_2$, —$NR^eS(O)R^e$, —$NR^eS(O)_2R^e$, —$NR^eS(O)N(R^e)_2$, —$NR^eS(O)_2N(R^e)_2$, —$SR^e$, —$S(O)R^e$, —$S(O)_2R^e$, —$S(O)N(R^e)_2$, or —$S(O)_2(NR^e)_2$, wherein q is 0, 1, 2, or 3;

$R^a$ and $R^b$, independently, are hydrogen, $C_{1-6}$alkoxy, $C_{3-8}$cycloalkyl, or a $C_{1-6}$alkyl optionally substituted with a substituent selected from the group consisting of cyano, halo, hydroxy, $C_{1-6}$alkoxy, and —$N(R^f)_2$, or $R^a$ and $R^b$ are taken together with the nitrogen to which they are attached to form a heterocyclyl ring;
$R^c$ is hydrogen, halo, $C_{1-6}$ alkyl, $C_{1-4}$acyl, $C_{1-4}$acyloxy, or —$N(R^g)_2$;
$R^d$ is hydrogen, halo, or $C_{1-6}$alkyl;
$R^e$, independently, is hydrogen, $C_{1-6}$alkyl, $C_{2-6}$alkenyl, $C_{2-6}$alkynyl, $C_{3-7}$cycloalkyl, $C_{6-14}$aryl, $C_{7-15}$aralkyl, heteroaryl, or heterocyclyl;
$R^f$, independently, is hydrogen or $C_{1-6}$alkyl; and
$R^g$, independently, is hydrogen or $C_{1-4}$acyl;
or a pharmaceutically acceptable salt thereof More particularly, the present invention is directed to compounds having a structural formula (II):

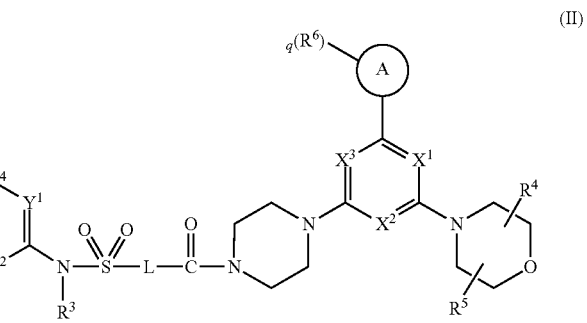

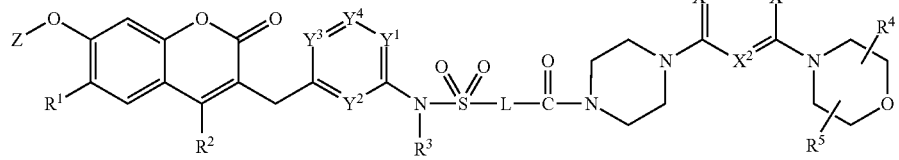

wherein Z is a heteroaryl group or $R^aR^bNCO$—;
$Y^1$ and $Y^2$, independently, are N or $CR^c$;
$Y^3$ and $Y^4$, same or different, are each $CR^d$;
$X^1$, $X^2$, and $X^3$, independently, are N or $CR^3$, wherein at least one of $X^1$, $X^2$, and $X^3$ is N;
A is cycloalkyl, heterocycyl, aryl, or heteroaryl;
L is $(CH_2)_n$, wherein n is an integer 3, 4, 5, 6, 7, 8, or 9, $(CH_2)_m\text{-}NH\text{-}(CH_2)_p$, wherein m and p, independently, are integers 0, 1, 2, 3, 4, 5, or 6, $(CH_2O)_l$, or $(CH_2CH_2O)_l$, wherein l is 5, 6, 7, 8, or 9;
$R^1$ is hydrogen, a halo, cyano, $C_{1-6}$alkyl, $C_{2-7}$alkenyl, carbamoyl, or $C_{2-7}$ alkynyl optionally substituted with a $C_{1-4}$acyl group;
$R^2$ is $C_{1-6}$alkyl optionally substituted with halo, OH, $C_{1-6}C(=O)R^a$, or $CH_2OC_{1-6}$ alkyl;
$R^3$ is hydrogen or $C_{1-6}$alkyl;
$R^4$ and $R^5$, independently are hydrogen or $C_{1-6}$alkyl, or $R^4$ and $R^5$ are taken together with the carbon to which they are bound to form $C_{1-6}$alkylene, $C_{1-6}$heteroalkylene, $C_{2-6}$alkenylene, or $C_{2-6}$heteroalkenylene;
$R^6$, independently, is cyano, halo, nitro, $C_{1-6}$alkyl, halo$C_{1-6}$ alkyl, $C_{2-6}$alkenyl, $C_{2-6}$alkynyl, $C_{3-7}$ cycloalkyl, $C_{6-14}$aryl, $C_{7-15}$ aralkyl, heteroaryl, heterocyclyl, —$C(O)R^e$, —$C(O)OR^e$, —$C(O)N(R^e)_2$, —$C(NR^e)N(R^e)_2$, —$OR^e$, —$OC(O)R^e$, —$OC(O)OR^e$, —$OC(O)N(R^e)_2$, —$OC(=NR^e)N(R^e)_2$, —$OS(O)R^e$, —$OS(O)_2R^e$, —$OS(O)N(R^e)_2$, —$OS(O)_2N(R^e)_2$, —$N(R^e)_2$, —$NR^eC(O)R^e$, —$NR^eC(O)N(R^e)_2$, —$NR^eC(=NR^e)N(R^e)_2$, —$NR^eS(O)R^e$, —$NR^eS(O)_2R^e$, —$NR^eS(O)N(R^e)_2$, —$NR^eS(O)_2N(R^e)_2$, —$SR^e$, —$S(O)R^e$, —$S(O)_2R^e$, —$S(O)N(R^e)_2$, or —$S(O)_2(NR^e)_2$, wherein q is 0, 1, 2, or 3;
$R^a$ and $R^b$, independently, are hydrogen, $C_{1-6}$alkoxy, $C_{3-8}$cycloalkyl, or a $C_{1-6}$alkyl optionally substituted with a substituent selected from the group consisting of cyano, halo, hydroxy, $C_{1-6}$alkoxy, and $-N(R^f)_2$, or $R^a$ and $R^b$ are taken together with the nitrogen to which they are attached to form a heterocyclyl ring;

$R^c$ is hydrogen, halo, $C_{1-6}$ alkyl, $C_{1-4}$acyl, $C_{1-4}$acyloxy, or $-N(R^g)_2$;

$R^d$ is hydrogen, halo, or $C_{1-6}$alkyl;

$R^e$, independently, is hydrogen, $C_{1-6}$alkyl, $C_{2-6}$alkenyl, $C_{2-6}$alkynyl, $C_{3-7}$cycloalkyl, $C_{6-14}$aryl, $C_{7-15}$ aralkyl, heteroaryl, or heterocyclyl;

$R^f$, independently, is hydrogen or $C_{1-6}$alkyl; and $R^g$, independently, is hydrogen or $C_{1-4}$acyl;

or a pharmaceutically acceptable salt thereof

In some embodiments, each of $X^1$, $X^2$, and $X^3$ is N. In other embodiments, the A ring system is a heteroaryl ring system, for example, benzimidazolyl. In other embodiments, the A ring system is substituted with a halo$C_{1-6}$alkyl group, for example $-CHF_2$.

In some embodiments, L is $-(CH_2)_{2,3}-NH-(CH_2)_{2-5}-$ or $-(CH_2)_{5-9}-$. In one embodiment, Z is $-C(=O)NR^aR^b$, for example $-C(=O)N(CH_3)_2$. In other embodiments, $R^3$ is $C_{1-6}$alkyl, for example, $CH_3-$ or $CH_3CH_2-$. In some embodiments, $Y^1$ and $Y^2$ each are $CR^c$ and $Y^3$ and $Y^4$ each are $CR^d$.

In one embodiment, the present invention provides a method of treating a condition or disease by administering a therapeutically effective amount of a compound of structural formula (I) to an individual in need thereof. The disease or condition of interest is treatable by inhibition of MEK and/or PI3K, for example, a cancer.

Another embodiment of the present invention is to provide a composition comprising (a) a dual MEK/PI3K inhibitor of structural formula (I) or (II) and (b) an excipient and/or pharmaceutically acceptable carrier useful in treating diseases or conditions wherein inhibition of MEK and/or PI3K provides a benefit.

Another embodiment of the present invention is to utilize a composition comprising a compound of structural formula (I) or (II) and a second therapeutically active agent in a method of treating an individual for a disease or condition wherein inhibition of MEK and/or PI3K provides a benefit.

In a further embodiment, the invention provides for use of a composition comprising a dual MEK/PI3K inhibitor of structural formula (I) or (II) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a dual MEK/PI3K inhibitor of structural formula (I) or (II), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The dual MEK/PI3K inhibitor of structural formula (I) or (II) and the second therapeutic agent can be administered together as a single-unit dose or separately as multi-unit doses, wherein the dual MEK/PI3K inhibitor of structural formula (I) or (II) is administered before the second therapeutic agent or vice versa. It is envisioned that one or more dose of a dual MEK/PI3K inhibitor of structural formula (I) or (II) and/or one or more dose of a second therapeutic agent can be administered.

In one embodiment, a dual MEK/PI3K inhibitor of structural formula (I) or (II) and a second therapeutic agent are administered simultaneously. In related embodiments, a dual MEK/PI3K inhibitor of structural formula (I) or (II) and second therapeutic agent are administered from a single composition or from separate compositions. In a further embodiment, the dual MEK/PI3K inhibitor of structural formula (I) or (II) and second therapeutic agent are administered sequentially. A dual MEK/PI3K inhibitor of structural formula (I) or (II), as used in the present invention, can be administered in an amount of about 0.005 to about 500 milligrams per dose, about 0.05 to about 250 milligrams per dose, or about 0.5 to about 100 milligrams per dose.

These and other embodiments and features of the present invention will become apparent from the following detailed description of the preferred embodiments.

DETAILED DESCRIPTION OF THE PREFERRED EMBODIMENTS

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "PI3K" as used herein means a Class I (including Class Ia and Class Ib), Class II, or Class III phosphonoinositide-3-kinase, as defined in U.S. Patent Publication No. 2011/0009405, incorporated herein by reference in its entirety.

The term "MEK" as used herein means mitogen-activated protein kinase.

The term "a disease or condition wherein inhibition of PI3K and/or MEK provides a benefit" pertains to a condition in which PI3K and/or MEK, and/or an action of PI3K and/or MEK, is important or necessary, e.g., for the onset, progress, expression of that disease or condition, or a disease or a condition which is known to be treated by a PI3K or MEK inhibitor (such as ZSTK474). An example of such a condition includes, but is not limited to, a cancer. One of ordinary skill in the art is readily able to determine whether a compound treats a disease or condition mediated by PI3K and/or MEK for any particular cell type, for example, by assays which conveniently can be used to assess the activity of particular compounds.

The term "second therapeutic agent" refers to a therapeutic agent different from a dual MEK/PI3K inhibitor of structural formula (I) or (II) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, compounds of structural formula (I) and (II) are potent inhibitors of MEK and PI3K and can be used in treating diseases and conditions wherein inhibition of MEK and/or PI3K provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce MEK and PI3K signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a dual MEK/PI3K inhibitor of structural formula (I) can be administered at the same time or sequentially in any order at different points in time as a second therapeutic agent. A present dual MEK/PI3K inhibitor and the second therapeutic agent can be administered separately, in any appropriate form and by any suitable route. When a present dual MEK/PI3K inhibitor and the second therapeutic agent are not administered concurrently, it is understood that they can be administered in any order to a subject in need thereof. For example, a present dual MEK/PI3K inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a dual MEK/PI3K inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Research has established that targeting MEK and PI3K using small molecule inhibitors is a viable cancer therapeutic strategy. However, cancers with KRAS mutation are known to be constitutively activated, refractory to standard of care, and a marker for poor prognosis. Two KRAS effector pathways, MAPK and PI3K, are important harbingers of proliferation and survival, respectively, and are mechanism of resistance for each other. Pre-clinical studies of cancers have shown that dual inhibition of MAPK and PI3K pathways have synergistic effects, which provides a rationale for combination therapies in a clinical setting.

The clinical relevance of these findings is currently being investigated in combination trials with MEK inhibitors administered with PI3K or AKT inhibitors (19). However, a non-promiscuous "single agent combination" drug offers a number of envisioned advantages over a rationally designed cocktail approach. First, off-target effects are compounded when combining two separate agents regardless of the selectivity of the individual components. Some off-target activities have proven advantageous for the treatment of unintended patient populations. For example, the "selective" abl kinase inhibitor imatinib has proven efficacious for the treatment of c-kit-driven GIST, as well as certain PDGFR-driven malignancies (20). However, in the greater number of instances, collateral damage in the form of non-mechanistic based toxicities occurs when unintended kinase targets are inhibited. Second, differing pharmacokinetic profiles between individual agents can be problematic when combining them in the clinic, which can be further compounded by differing drug-drug interaction liabilities. Issues of patient compliance and drug costs further support the design of single chemical entities to impair signaling through multiple nodes. Logistical hurdles also are encountered when conducting combination trials with two unapproved agents. While clinical data with the MEK inhibitor trametinib looks encouraging (21, 22), it is less likely that a PI3K or AKT inhibitor will be approved in the foreseeable future. Tumor cells are displaying a wide array of mechanisms to restore flux through the PI3K/AKT/mTOR pathway when challenged with a PI3K inhibitor, thereby limiting their single agent effectiveness and hindering their regulatory approval path (23). Favorable efficacy derived from horizontal, i.e. parallel, inhibitor of PI3K/AKT and MEK/ERK signaling, compared to single step targeting, has been borne out in early clinical data (19).

The present compounds are the first examples of chemically-linked dual inhibitors to specifically target both the MAPK and PI3K pathways. A single molecule having this combined pathway inhibition capability increases efficacy and safety over individual mono-targeting inhibitors. Administration of a single drug, as opposed to two drugs, also increases patient compliance with a prescribed treatment regimen.

The present invention is directed to new class of dual inhibitors of MEK and PI3K. The dual MEK/PI3K inhibitors of the present invention therefore are useful in the treatment of cancers and precancers in subjects in need of such treatment. Also provided are methods of treating a subject comprising administering a therapeutically effective amount of a present compound to a subject in need of such treatment.

The present invention is directed to dual MEK/PI3K inhibitors having a structural formula (I):

The present invention is directed to compounds having the following structural formula (I):

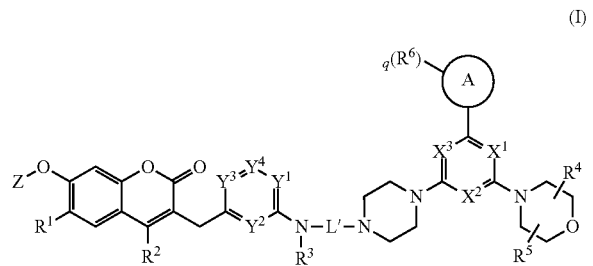

(I)

wherein Z is a heteroaryl group or $R^aR^bNCO—$;
$Y^1$ and $Y^2$, independently, are N or $CR^c$;

$Y^3$ and $Y^4$, same or different, are each $CR^d$;
$X^1$, $X^2$, and $X^3$, independently, are N or $CR^3$, wherein at least one of $X^1$, $X^2$, and $X^3$ is N;
A is cycloalkyl, heterocycyl, aryl, or heteroaryl;
L' is J-$(CH_2)_n$—K, wherein n is an integer 3, 4, 5, 6, 7, 8, or 9, J-$(CH_2)_m$—N($R^7$)—$(CH_2)_p$—K, wherein m and p, independently, are integers 0, 1, 2, 3, 4, 5, or 6, and $R^7$ is H, methyl, ethyl, propyl or butyl,
$(CH_2O)_l$, $(CH_2CH_2O)_l$, wherein l is 5, 6, 7, 8, or 9, or
—(NHCHRC(═O)—$)_q$, wherein R, independently, is an amino acid residue, and q is an integer 3, 4, 5, 6, 7, 8, or 9;
J and K, independently, are (—C(═O)—, —C(═O)N—, —SO$_2$—, or —CH$_2$—;
$R^1$ is hydrogen, a halo, cyano, $C_{1-6}$alkyl, $C_{2-7}$alkenyl, carbamoyl, or $C_{2-7}$ alkynyl optionally substituted with a $C_{1-4}$acyl group;
$R^2$ is $C_{1-6}$alkyl optionally substituted with halo, OH, $C_{1-6}C(═O)R^a$, or $CH_2OC_{1-6}$ alkyl;
$R^3$ is hydrogen or $C_{1-6}$alkyl;
$R^4$ and $R^5$, independently are hydrogen or $C_{1-6}$alkyl, or $R^4$ and $R^5$ are taken together with the carbon to which they are bound to form $C_{1-6}$alkylene, $C_{1-6}$heteroalkylene, $C_{2-6}$alkenylene, or $C_{2-6}$heteroalkenylene;
$R^6$, independently, is cyano, halo, nitro, $C_{1-6}$alkyl, halo$C_{1-6}$ alkyl, $C_{2-6}$alkenyl, $C_{2-6}$alkynyl, $C_{3-7}$cycloalkyl, $C_{6-14}$aryl, $C_{7-15}$aralkyl, heteroaryl, heterocyclyl, —C(O)$R^e$, —C(O)O$R^e$, —C(O)N($R^e$)$_2$, —C(N$R^e$)N($R^e$)$_2$, —O$R^e$, —OC(O)$R^e$, —OC(O)O$R^e$, —OC(O)N($R^e$)$_2$, —OC(═N$R^e$)N($R^e$)$_2$, —OS(O)$R^e$, —OS(O)$_2R^e$, —OS(O)N($R^e$)$_2$, —OS(O)$_2$N($R^e$)$_2$, —N($R^e$)$_2$, —N$R^e$C(O)$R^e$, —N$R^e$C(O)N($R^e$)$_2$, —N$R^e$C(═N$R^e$)N($R^e$)$_2$, —N$R^e$S(O)$R^e$, —N$R^e$S(O)$_2R^e$, —N$R^e$S(O)N($R^e$)$_2$, —N$R^e$S(O)$_2$N($R^e$)$_2$, —S$R^e$, —S(O)$R^e$, —S(O)$_2R^e$, —S(O)N($R^e$)$_2$, or —S(O)$_2$(N$R^e$)$_2$, wherein q is 0, 1, 2, or 3;
$R^a$ and $R^b$, independently, are hydrogen, $C_{1-6}$alkoxy, $C_{3-8}$cycloalkyl, or a $C_{1-6}$alkyl optionally substituted with a substituent selected from the group consisting of cyano, halo, hydroxy, $C_{1-6}$alkoxy, and —N($R^f$)$_2$, or $R^a$ and $R^b$ are taken together with the nitrogen to which they are attached to form a heterocyclyl ring;
$R^c$ is hydrogen, halo, $C_{1-6}$ alkyl, $C_{1-4}$acyl, $C_{1-4}$acyloxy, or —N($R^g$)$_2$;
$R^d$ is hydrogen, halo, or $C_{1-6}$alkyl;
$R^e$, independently, is hydrogen, $C_{1-6}$alkyl, $C_{2-6}$alkenyl, $C_{2-6}$alkynyl, $C_{3-7}$cycloalkyl, $C_{6-14}$aryl, $C_{7-15}$aralkyl, heteroaryl, or heterocyclyl;
$R^f$, independently, is hydrogen or $C_{1-6}$alkyl; and
$R^g$, independently, is hydrogen or $C_{1-4}$acyl;
or a pharmaceutically acceptable salt thereof
In another embodiment, the dual MEK/PI3K inhibitor has a structural formula (II).

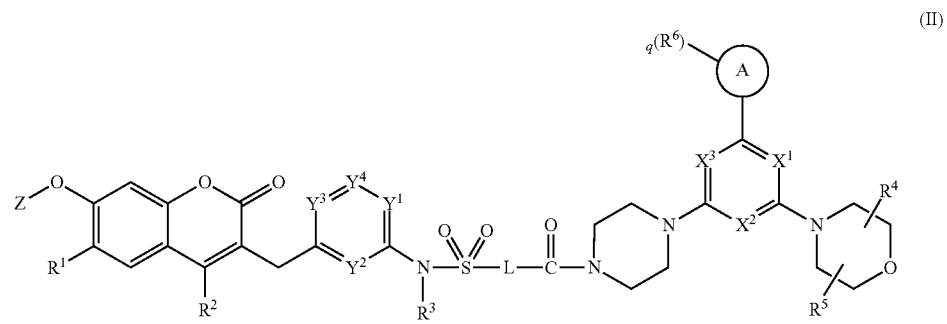

(II)

wherein Z is a heteroaryl group or $R^aR^bNCO-$;

$Y^1$ and $Y^2$, independently, are N or $CR^c$;

$Y^3$ and $Y^4$, same or different, are each $CR^d$;

$X^1$, $X^2$, and $X^3$, independently, are N or $CR^3$, wherein at least one of $X^1$, $X^2$, and $X^3$ is N;

A is cycloalkyl, heterocycyl, aryl, or heteroaryl;

L is $(CH_2)_n$, wherein n is an integer 3, 4, 5, 6, 7, 8, or 9, $(CH_2)_m-NH-(CH_2)_p$, wherein m and p, independently, are integers 0, 1, 2, 3, 4, 5, or 6, or $(CH_2O)_l$, or $(CH_2CH_2O)_l$, wherein l is 5, 6, 7, 8, or 9;

$R^1$ is hydrogen, a halo, cyano, $C_{1-6}$alkyl, $C_{2-7}$alkenyl, carbamoyl, or $C_{2-7}$ alkynyl optionally substituted with a $C_{1-4}$acyl group;

$R^2$ is $C_{1-6}$alkyl optionally substituted with a halo, OH, $C_{1-6}C(=O)R^a$, or $CH_2OC_{1-6}$ alkyl;

$R^3$ is hydrogen or $C_{1-6}$alkyl;

$R^4$ and $R^5$, independently are hydrogen or $C_{1-6}$alkyl, or $R^4$ and $R^5$ are taken together with the carbon to which they are bound to form $C_{1-6}$alkylene, $C_{1-6}$heteroalkylene, $C_{2-6}$alkenylene, or $C_{2-6}$heteroalkenylene;

$R^6$, independently, is cyano, halo, nitro, $C_{1-6}$ alkyl, halo$C_{1-6}$ alkyl, $C_{2-6}$ alkenyl, $C_{2-6}$alkynyl, $C_{3-7}$cycloalkyl, $C_{6-14}$aryl, $C_{7-15}$aralkyl, heteroaryl, heterocyclyl, $-C(O)R^e$, $-C(O)OR^e$, $-C(O)N(R^e)_2$, $-C(NR^e)N(R^e)_2$, $-OR^e$, $-OC(O)R^e$, $-OC(O)OR^e$, $-OC(O)N(R^e)_2$, $-OC(=NR^e)N(R^e)_2$, $-OS(O)R^e$, $-OS(O)_2R^e$, $OS(O)N(R^e)_2$, $-OS(O)_2N(R^e)_2$, $-N(R^e)_2$, $-NR^eC(O)R^e$, $-NR^eC(O)N(R^e)_2$, $-NR^eC(=NR^e)N(R^e)_2$, $-NR^eS(O)R^e$, $-NR^eS(O)_2R^e$, $-NR^eS(O)N(R^e)_2$, $-NR^eS(O)_2N(R^e)_2$, $-SR^e$, $-S(O)R^e$, $-S(O)_2R^e$, $-S(O)N(R^e)_2$, or $-S(O)_2(NR^e)_2$, wherein q is 0, 1, 2, or 3;

$R^a$ and $R^b$, independently, are hydrogen, $C_{1-6}$alkoxy, $C_{3-8}$cycloalkyl, or a $C_{1-6}$alkyl optionally substituted with a substituent selected from the group consisting of cyano, halo, hydroxy, $C_{1-6}$alkoxy, and $-N(R^f)^2$, or $R^a$ and $R^b$ are taken together with the nitrogen to which they are attached to form a heterocyclyl ring;

$R^c$ is hydrogen, halo, $C_{1-6}$ alkyl, $C_{1-4}$ acyl, $C_{1-4}$ acyloxy, or $-N(R^g)_2$;

$R^d$ is hydrogen, halo, or $C_{1-6}$ alkyl;

$R^e$, independently, is hydrogen, $C_{1-6}$alkyl, $C_{2-6}$alkenyl, $C_{2-6}$alkynyl, $C_{3-7}$cycloalkyl, $C_{6-14}$aryl, $C_{7-15}$ aralkyl, heteroaryl, or heterocyclyl;

$R^f$, independently, is hydrogen or $C_{1-6}$alkyl; and $R^g$, independently, is hydrogen or $C_{1-4}$acyl;

or a pharmaceutically acceptable salt thereof

The compounds of structural formula (I) and (II) inhibit MEK and PI3K and are useful in the treatment of a variety of diseases and conditions. In particular, the compounds of structural formula (I) and (II) are used in methods of treating a disease or condition wherein inhibition of MEK and/or PI3K provides a benefit, for example, cancers. The method comprises administering a therapeutically effective amount of a compound of structural formula (I) or (II) to an individual in need thereof. The present methods also encompass administering a second therapeutic agent to the individual in addition to the compound of structural formula (I) or (II). The second therapeutic agent is selected from drugs known as useful in treating the disease or condition afflicting the individual in need thereof, e.g., a chemotherapeutic agent and/or radiation known as useful in treating a particular cancer.

As used herein, the term "alkyl" refers to straight chained and branched saturated $C_{1-10}$ hydrocarbon groups including, but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term $C_n$ means the alkyl group has "n" carbon atoms. The term $C_{n-m}$ means that alkyl groups can have from "n" to "m" carbon atoms. The term "alkylene" refers to an alkyl group having a substituent. An alkyl, e.g., methyl, or alkylene, e.g., $-CH_2-$, group can be substituted with halo, trifluoromethyl, trifluoromethoxy, hydroxy, alkoxy, nitro, cyano, alkylamino, or amino groups, for example.

The term "halo$C_{1-6}$alkyl" refers to a $C_{1-6}$alkyl group substituted with one or more, and typically one to five, halo groups. Specific nonlimiting examples of a $C_{1-6}$alkyl group substituted with a halogen atom, includes, but are not limited to, fluoromethyl, difluoromethyl, trifluoromethyl, fluoroethyl, difluoroethyl, trifluoroethyl, pentafluoroethyl, fluoropropyl, difluoropropyl, trifluoropropyl, heptafluoropropyl, fluorobutyl, difluorobutyl, trifluorobutyl, fluoropentyl, difluoropentyl, trifluoropentyl, tetrafluoropentyl, fluoroheptyl, difluoroheptyl, trifluoroheptyl, tetrafluoroheptyl, pentafluoroheptyl, chloromethyl, dichloromethyl, trichloromethyl, chloroethyl, dichloroethyl, trichloroethyl, pentachloroethyl, chloropropyl, dichloropropyl, trichloropropyl, heptachloropropyl, chlorobutyl, dichlorobutyl, trichlorobutyl, chloropentyl, dichloropentyl, trichloropentyl, tetrachloropentyl, chloroheptyl, dichloroheptyl, trichloroheptyl, tetrachloroheptyl, pentachloroheptyl, bromomethyl, dibromomethyl, tribromomethyl, bromoethyl, dibromoethyl, tribromoethyl, pentabromoethyl, bromopropyl, dibromopropyl, tribromopropyl, heptabromopropyl, bromobutyl, dibromobutyl, tribromobutyl, bromopentyl, dibromopentyl, tribromopentyl, tetrabromopentyl, bromoheptyl, dibromoheptyl, tribromoheptyl, tetrabromoheptyl, pentabromoheptyl, iodomethyl, diiodomethyl, triiodomethyl, iodoethyl, diiodoethyl, triiodoethyl, pentaiodoethyl, iodopropyl, diiodopropyl, triiodopropyl, heptaiodopropyl, iodobutyl, diiodobutyl, triiodobutyl, iodopentyl, diiodopentyl, triiodopentyl, tetraiodopentyl, iodoheptyl, diiodoheptyl, triiodoheptyl, tetraiodoheptyl, and pentaiodoheptyl.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkynyl" and "alkynylene" are defined identically as "alkyl" and "alkylene" except the group contains a carbon-carbon triple bond. Nonlimiting examples of alkenyl and alkynyl are vinyl, allyl, 1-butenyl, 2-butenyl, 3-butenyl, pentenyl, pentadienyl, hexenyl, hexadienyl, heptenyl, heptatrienyl, ethynyl, 1-propynyl, 2-propynyl, 1-butyryl, 2-butyryl, 3-butynyl, pentynyl, pentadiynyl, hexynyl, hexadiynyl, heptynyl, heptadiynyl, and heptatriynyl.

As used herein, the term "halo" is defined as fluoro, chloro, bromo, and iodo.

The term "$C_{1-4}$acyl" is defined as $R-C(=O)-$ containing a total of 1 to 4 carbon atoms, e.g., formyloxy, acetyloxy, n-propionyloxy, i-propionyloxy, butyryloxy, and secbutyryloxy (isobutyryloxy).

The term "hydroxy" is defined as $-OH$.

The term "alkoxy" is defined as $-OR$, wherein R is alkyl.

The term "amino" is defined as $-NH_2$, and the term "alkylamino" is defined as $-NR_2$, wherein at least one R is alkyl and the second R is alkyl or hydrogen.

The term "nitro" is defined as $-NO_2$.

The term "cyano" is defined as $-CN$.

The term "carbamoyl" is defined as $-C(=O)NR_2$.

The term "trifluoromethyl" is defined as $-CF_3$.

The term "trifluoromethoxy" is defined as $-OCF_3$.

As used herein, groups such as

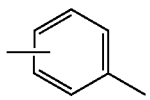

is an abbreviation for

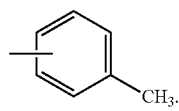

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, in which one of the rings is aromatic and the other ring(s) can be saturated, partially unsaturated, or aromatic, for example, dihydronaphthyl, indenyl, indanyl, or tetrahydronaphthyl (tetralinyl).

The term "aralkyl" refers to monovalent alkyl group substituted with aryl. An aryl group or aralkyl group optionally is substituted with one or more, typically one to four groups disclosed in U.S. Patent Publication No. 2011/0009405, incorporated herein by reference. For example, an aryl or aralkyl group can be unsubstituted or substituted with one or more nonlimiting groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can containing one or two O atoms, one or two S atoms, and/or one to four N atoms, provided that the total number of heteroatoms in each ring is four or less and each ring contains at least one carbon atom. In some embodiments, the heteroaryl ring system has 5 to 20, 5 to 15, or 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl ring systems include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl. Additional heteroaryl substituents are disclosed in U.S. Patent Publication No. 2011/0009405, incorporated herein by reference.

As used herein, the term "cycloalkyl" means a monocyclic aliphatic ring containing three to eight carbon atoms, including cyclopropyl, cyclobutyl, cyclopentyl, cyclohexyl, cycloheptyl, and cyclooctyl, optionally substituted with groups disclosed in U.S. Patent Publication No. 2011/0009405, incorporated herein by reference.

As used herein, the term "heterocycyl" means a monocyclic or a bicyclic aliphatic ring containing 4 to 12 total atoms, of which one to five of the atoms are independently selected from nitrogen, oxygen, and sulfur, and the remaining atoms are carbon. Nonlimiting examples of heterocycyl groups are azetidinyl, pyrrolidinyl, piperidinyl, piperazinyl, pyrrolyl, dihydropyrrolyl, dihydropyridinyl, morpholinyl, thiomorpholinyl, tetrahydrofuryl, tetrahydrothienyl, dioxolanyl, oxathiolanyl, dioxanyl, oxacycloheptyl, dioxacycloheptyl, thiacycloheptyl, and diazacycloheptyl, each optionally substituted with halo, C$_{1-6}$alkyl, C$_{1-6}$alkoxy, cyano, amino, carbamoyl, nitro, carboxy, C$_{2-7}$ alkenyl, C$_{2-7}$ alkynyl, or the like on an atom of the ring.

As used herein, the term "heteroalkylene" refers to an optionally substituted linear or branched saturated divalent hydrocarbon radical that contains one or more heteroatoms each independently selected from O, S, and N in the hydrocarbon chain. A C$_{1-6}$heteroalkylene refers to a linear saturated divalent hydrocarbon radical of 1 to 6 carbon atoms or a branched saturated divalent hydrocarbon radical of 3 to 6 carbon atoms. Nonlimiting examples of heteroalkylene groups include —CH$_2$O—, —CH$_2$OCH$_2$—, —CH$_2$CH$_2$O—, —CH$_2$NH—, —CH$_2$NHCH$_2$—, —CH$_2$CH$_2$NH—, —CH$_2$S—, —CH$_2$SCH$_2$—, and —CH$_2$CH$_2$S—.

As used herein, the term "heteroalkenylene" refers to an optionally substituted linear or branched divalent hydrocarbon radical, which contains one or more, in one embodiment, one to five, in another embodiment, one, carbon-carbon double bond(s), and which contains one or more heteroatoms each independently selected form O, S, and N in the hydrocarbon chain. "C$_{2-6}$heteroalkenylene" refers to a linear unsaturated divalent hydrocarbon radical of 2 to 6 carbon atoms or a branched unsaturated divalent hydrocarbon radical of 3 to 6 carbon atoms. Nonlimiting examples of heteroalkenylene groups include —CH═CHO—, —CH═CHOCH$_2$—, —CH═CHCH$_2$O—, —CH═CHS—, —CH═CHSCH$_2$—, —CH═CHCH$_2$S—, and —CH═CHCH$_2$NH—. Heteroalkylene and heteroalkenylene groups are optionally substituted with groups disclosed in U.S. Patent Publication No. 2011/0009405, incorporated herein by reference.

As used herein, the term "an amino acid residue" means a residue of histidine, alanine, isoleucine, arginine, leucine, aspartic acid, lysine, cysteine, methionine, glutamic acid, phenylalanine, glutamine, threonine, glycine, tryptophan, proline, valine, serine, tyrosine, or asparagine.

In accordance with the present invention, ring B is phenyl or a five- or six-membered aromatic ring in which one to four of the carbon atoms, independently, are replaced by nitrogen, oxygen, or sulfur. In one preferred embodiment, ring B is phenyl. In other preferred embodiments, ring B is phenyl substituted with one or more halo group.

In preferred embodiments, Z is —C(═O)N(CH$_3$)$_2$ or

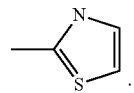

In other preferred embodiments,

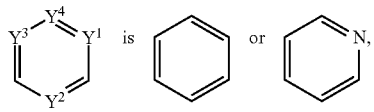

either optionally substituted. A preferred substituent on the ring is halo, most preferably fluoro.

In other preferred embodiments,

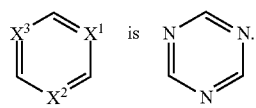

In preferred embodiments, the A ring system is heterocycyl. Nonlimiting examples of A rings, include, but are not limited to, optionally substituted:

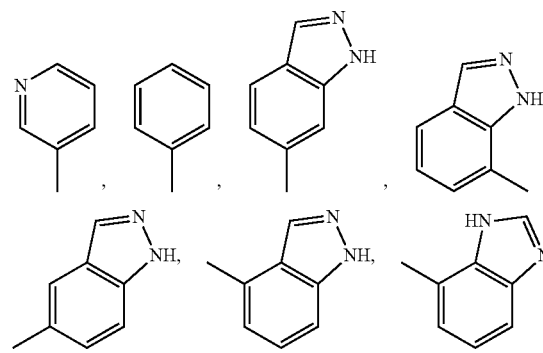

Examples of substituents include, but are not limited to, one or more of —OH, —OCH₃, —NH₂, —CH₂—OH, —NHC(=O)NH₂, —NHC(=O)NHC$_{1-3}$alkyl, —NH—C(=O)C$_{1-3}$ alkyl, —NHSO₂C$_{1-3}$ alkyl, and haloC$_{1-6}$alkyl.

In some specific embodiments, the A ring is

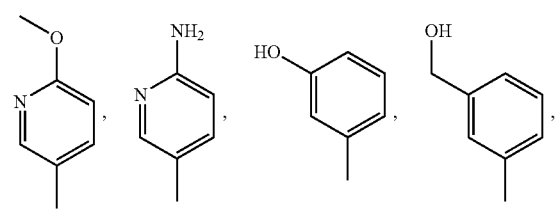

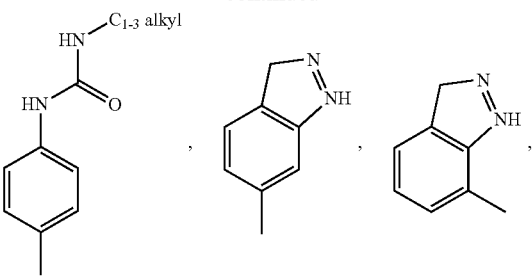

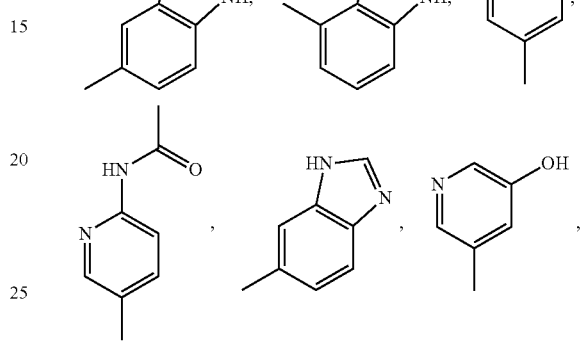

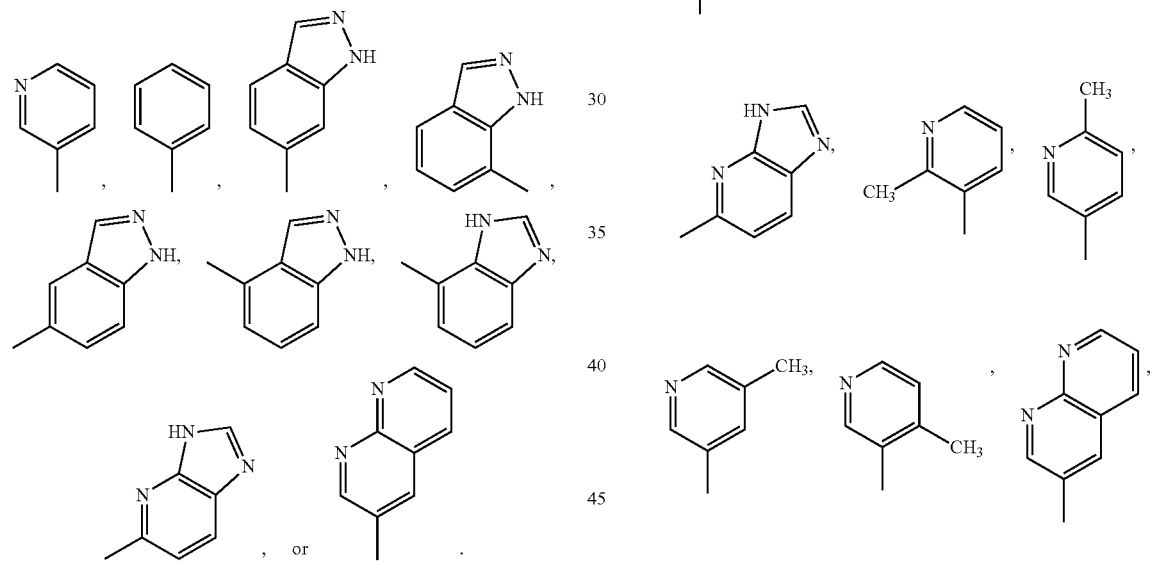

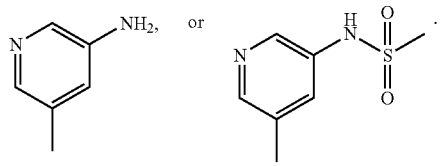

In one embodiment the A ring preferably is optionally substituted

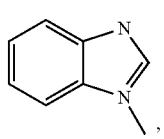

and in a more preferred embodiment is

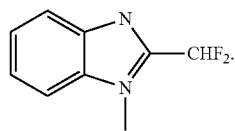

In some preferred embodiments, $R^3$ is H, $CH_3$, or $CH_3CH_2$. In additional preferred embodiments, L is —$(CH_2)_3NH(CH_2)_5$— or —$(CH_2)_9$—.

In some embodiments, Z is $(CH_3)_2NC(=O)$, 2-N-methylimidazolyl, 2-pyrimidinyl, 2-thiazolyl, 3-thienyl, 2-pyridinyl, 3-pyridinyl, 4-pyridinyl, 2-benzothiazolyl,

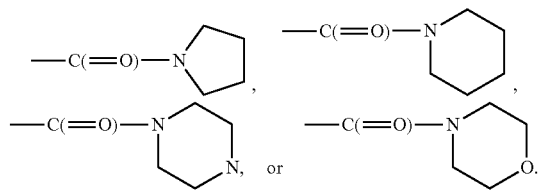

In other embodiments, $R^1$ is $CH_3$, F, Cl, I, CN, or $C(=O)NH_2$.

In yet other embodiments, $R^2$ is $CH_3$, $CH_2CH_3$, $CH_2F$, $CH_2Br$, $CH_2CH_2OH$, $CH_2CH(CH_3)OH$, $CH_2C(=O)CH_3$, $CH_2C(=O)OCH_3$, $CH_2C(=O)OH$, $CH_2C(=O)NH_2$, $CH_2C(=O)N(CH_3)_2$, or $CH_2OCH_3$.

Additionally, salts, hydrates, and solvates of the present compounds also are included in the present invention and can be used in the methods disclosed herein. The present invention further includes all possible stereoisomers and geometric isomers of the compounds of structural formula (I) or (II). The present invention includes both racemic compounds and optically active isomers. When a compound of structural formula (I) or (II) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) or (II) are possible, the present invention is intended to include all tautomeric forms of the compounds.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I) or (II). Salts of compounds of formula (I) or (II) can be prepared during the final isolation and purification of the compounds or separately by reacting the compound with an acid having a suitable cation. The pharmaceutically acceptable salts of compounds of structural formula (I) or (II) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) or (II) as well as pharmaceutically acceptable salts, hydrates, or solvates thereof Specific compounds of the present invention include, but are not limited to, compounds having the structures set forth below.

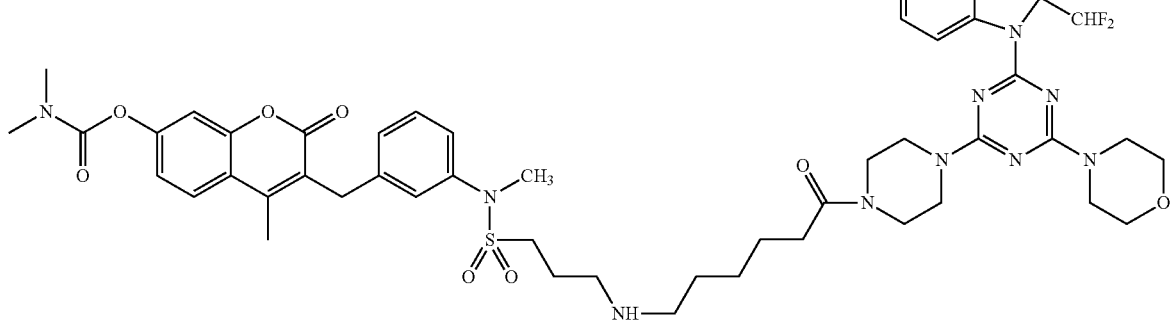

-continued

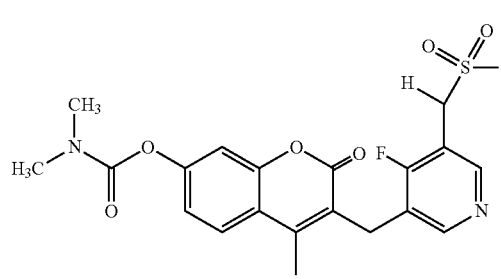 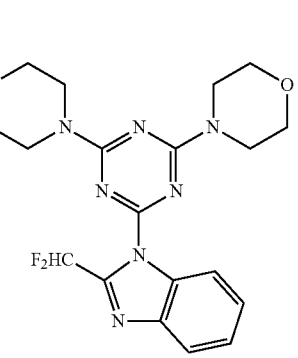

The present invention provides dual MEK/PI3K inhibitors, as exemplified by compounds of structural formula (I), for the treatment of diseases and conditions wherein inhibition of MEK and/or PI3K has a beneficial effect. In one embodiment, the present invention relates to a method of treating an individual suffering from a disease or condition wherein inhibition of the MEK or PI3K, and preferably both, provides a benefit comprising administering a therapeutically effective amount of a compound of structural formula (I) or (II) to an individual in need thereof. It is envisioned that a compound of structural formula (I) or (II) exhibits a greater activity against KRAS mutant tumors than either an MEK or PI3K inhibitor monotherapy.

The method of the present invention can be accomplished by administering a compound of structural formula (I) or (II) as the neat compound or as a pharmaceutical composition. Administration of a pharmaceutical composition, or neat compound of structural formula (I) or (II), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) or (II) and, optionally, a second therapeutic agent useful in the treatment of diseases and conditions wherein inhibition of dual MEK and/or PI3K provides a benefit, packaged separately or together, and an insert having instructions for using these active agents.

In many embodiments, a compound of structural formula (I) or (II) is administered in conjunction with a second therapeutic agent useful in the treatment of a disease or condition wherein inhibition of MEK and/or PI3K provides a benefit. The second therapeutic agent is different from the compound of structural formula (I) or (II). A compound of structural formula (I) or (II) and the second therapeutic agent can be administered simultaneously or sequentially to achieve the desired effect. In addition, the compound of structural formula (I) or (II) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) or (II) and the second therapeutic agent can be administered together as a single-unit dose or separately as multi-unit doses, wherein the compound of structural formula (I) or (II) is administered before the second therapeutic agent or vice versa. One or more dose of the compound of structural formula (I) or (II) and/or one or more dose of the second therapeutic agent can be administered. The compounds of structural formula (I) or (II) therefore can be used in conjunction with one or more second therapeutic agents, for example, but not limited to, anticancer agents.

The diseases and conditions that can be treated in accordance to the invention include, for example, cancers. A variety of cancers can be treated including, but not limited to: carcinomas, including bladder (including accelerated and metastic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the dual MEK/PI3K inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

The compounds of structural formula (I) are particularly useful in the treatment of pancreatic and colorectal cancers.

Additional diseases and conditions, including cancers, inflammatory diseases, allergic diseases, inflammatory bowel diseases, vasculitis, Behçet's syndrome, psoriasis, inflammatory dermatoses, asthma, respiratory allergic diseases, autoimmune diseases, graft rejection, fever, cardiovascular disorders, cerebrovascular disorders, fibrosis, connective tissue disease, sarcoidosis, genital and reproductive disorders, gastrointestinal disorders, neurologic disorders, sleep disorders, pain, renal disorders, and infections diseases, including HIV, that can be treated by administration of a present MEK and/or PI3K inhibitor are disclosed in U.S. Patent Publication No. 2011/0053907; U.S. Pat. No. 7,897,792; U.S. Patent Publication No. 2011/0009405, and U.S. Patent Publication No. 2010/0249099, each incorporated herein by reference in its entirety.

In the present method, a therapeutically effective amount of one or more compound (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) or (II) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) or (II) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) or (II) that is sufficient to maintain therapeutic effects.

Toxicity and therapeutic efficacy of the compounds of structural formula (I) or (II) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g., inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) or (II) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the dual MEK/PI3K inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present dual MEK/PI3K inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formula (I) or (II) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) or (II) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a dual MEK/PI3K inhibitor of structural formula (I), or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a compound of structural formula (I) or (II) can be administered with a chemotherapeutic agent and/or radiation.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present dual MEK/PI3K inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a dual MEK/PI3K inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof Examples of chemotherapeutic agents useful in a method of the present invention are listed in the following table.

TABLE 1

| Alkylating agents | Natural products |
|---|---|
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| uracil mustard | vinorelbine |
| temozolomide | vindesine |
| Nitrosoureas | Taxotere ® (docetaxel) |
| carmustine (BCNU) | estramustine |
| lomustine (CCNU) | estramustine phosphate |
| semustine (methyl-CCNU) | Epipodophylotoxins |
| chlormethine | etoposide |
| streptozocin | teniposide |
| Ethylenimine/Methyl-melamine | Antibiotics |
| triethylenemelamine (TEM) | actimomycin D |
| triethylene thiophosphoramide | daunomycin (rubidomycin) |
| (thiotepa) | doxorubicin (adriamycin) |
| hexamethylmelamine | mitoxantroneidarubicin |
| (HMM, altretamine) | bleomycin |
| Alkyl sulfonates | splicamycin (mithramycin) |
| busulfan | mitromycin-C |
| pipobroman | dactinomycin |
| Triazines | aphidicolin |
| dacarbazine (DTIC) | epirubicin |
| Antimetabolites | idarubicin |
| Folic Acid analogs | daunorubicin |
| methotrexate | mithramycin |
| trimetrexate | deoxy co-formycin |
| pemetrexed | Enzymes |
| (Multi-targeted antifolate) | L-asparaginase |
| Pyrimidine analogs | L-arginase |
| 5-fluorouracil | Radiosensitizers |
| fluorodeoxyuridine | metronidazole |
| gemcitabine | misonidazole |
| cytosine arabinoside | desmethylmisonidazole |
| (AraC, cytarabine) | pimonidazole |
| 5-azacytidine | etanidazole |
| 2,2'-difluorodeoxy-cytidine | nimorazole |
| floxuridine | RSU 1069 |
| pentostatine | EO9 |
| Purine analogs | RB 6145 |
| 6-mercaptopurine | Nonsteroidal antiandrogens |
| 6-thioguanine | SR4233 |
| azathioprine | flutamide |
| 2'-deoxycoformycin | nicotinamide |
| (pentostatin) | 5-bromodeozyuridine |
| erythrohydroxynonyl-adenine (EHNA) | 5-iododeoxyuridine |
| fludarabine phosphate | bromodeoxycytidine |
| 2-chlorodeoxyadenosine | Miscellaneous agents |
| (cladribine, 2-CdA) | Platinum coordination |
| Type I Topoisomerase Inhibitors | complexes |
| camptothecin | cisplatin |
| topotecan | carboplatin |
| irinotecan | oxaliplatin |
| Biological response modifiers | anthracenedione |
| G-CSF | mitoxantrone |
| GM-CSF | Substituted urea |
| Differentiation Agents | hydroxyurea |
| retinoic acid derivatives | Methylhydrazine derivatives |
| Hormones and antagonists | N-methylhydrazine (MIH) |
| Adrenocorticosteroids/antagonists | procarbazine |
| prednisone and equivalents | Adrenocortical suppressant |

TABLE 1-continued

| | |
|---|---|
| dexamethasone | mitotane (o,p'-DDD) |
| ainoglutethimide | ainoglutethimide |
| Progestins | Cytokines |
| hydroxyprogesterone caproate | interferon ($\alpha$, $\beta$, $\gamma$) |
| medroxyprogesterone acetate | interleukin-2 |
| megestrol acetate | Photosensitizers |
| Estrogens | hematoporphyrin derivatives |
| diethylstilbestrol | PHOTOFRIN ® |
| ethynyl estradiol/equivalents | benzoporphyrin derivatives |
| Antiestrogen | Npe6 |
| tamoxifen | tin etioporphyrin (SnET2) |
| Androgens | pheoboride-a |
| testosterone propionate | bacteriochlorophyll-a |
| fluoxymesterone/equivalents | naphthalocyanines |
| Antiandrogens | phthalocyanines |
| flutamide | zinc phthalocyanines |
| gonadotropin-releasing | Radiation |
| hormone analogs | X-ray |
| leuprolide | ultraviolet light |
| | gamma radiation |
| | visible light |
| | infrared radiation |
| | microwave radiation |

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274: 2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-$\alpha$-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer Inhibitors of the transduction of cellular proliferative signals are cytostatic agents. Representative examples include epidermal growth factor inhibitors, Her-2 inhibitors, PI3 inhibitors, Src kinase inhibitors, and PDGF inhibitors.

Additional second therapeutic agents that can be administered with a dual MEK/PI3K inhibitor of the present invention are well known in the art, for example as disclosed in U.S. Patent Publication 2011/0053907; and U.S. Patent Publication No. 2011/0009405, and U.S. Patent Publication No. 2010/0249099, each incorporated herein by reference in its entirety.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I) or (II).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) or (II) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I) or (II). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I) or (II).

When a therapeutically effective amount of a compound of structural formula (I) or (II) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) or (II) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) or (II) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) or (II) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) or (II) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) or (II) also can be formulated in rectal compositions, such as suppositories or retention enemas, e.g., containing conventional suppository bases. In addition to the formulations described previously, the compound of structural formula (I) or (II) also can be formulated as a depot preparation. Such long-acting formulations can be administered by implantation (for example, subcutaneously or intramuscularly) or by intramuscular injection. Thus, for example, the compounds of structural formula (I) or (II) can be formulated with suitable polymeric or hydrophobic materials (for example, as an emulsion in an acceptable oil) or ion exchange resins.

In particular, the compounds of structural formula (I) or (II) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) or (II) also can be injected parenterally, for example, intravenously, intramuscularly, subcutaneously, or intracoronarily. For parenteral administration, the dual MEK/PI3K inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) or (II) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior MEK and PI3K inhibitors possessed properties that hindered their development as therapeutic agents. In accordance with an important feature of the present invention, compounds of structural formula (I) or (II) were synthesized and evaluated as dual inhibitors for MEK and PI3K. It is envisioned that the compounds of structural formula (I) or (II) are more efficacious and less toxic than a combination therapy using an MEK inhibitor and a PI3K inhibitor.

SYNTHESIS OF COMPOUNDS

The present compounds are a result of conjugating, or linking, a coumarin-based MEK inhibitor with a triazine-based PI3K inhibitor to arrive at the dual MEK-PI3K inhibitors of the present invention. Coumarin-based MEK inhibitors are synthesized, for example, as disclosed in U.S. Pat. No. 7,897,792, incorporated herein by reference in its entirety. Triazine-based inhibitors are synthesized as disclosed in U.S. Patent Publication Nos. 2011/0053907, 2011/0009405, and 2010/0249099, each incorporated herein by reference in its entirety.

The MEK and PI3K inhibitors can be conjugated using the non-limiting approaches set forth in Scheme I.

Scheme I MEK and PI3K Binding Templates

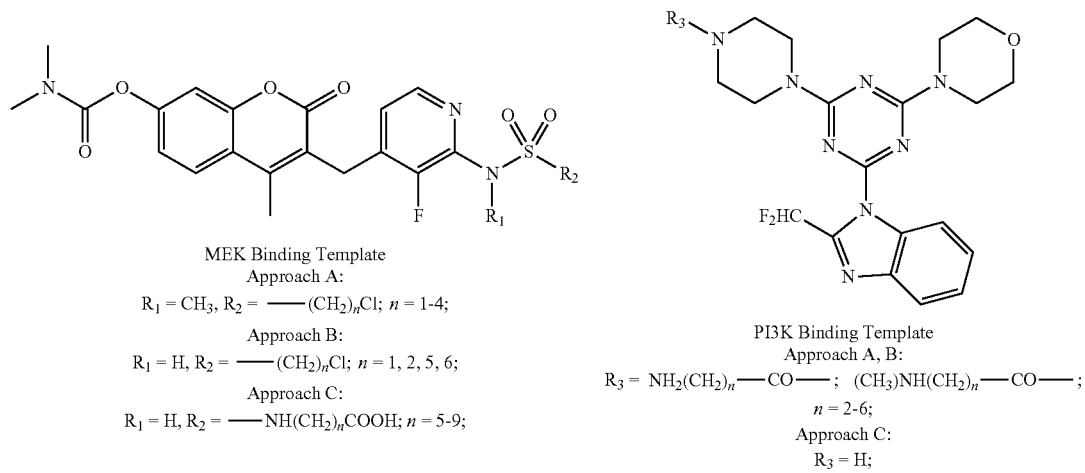

MEK Binding Template
Approach A:
$R_1 = CH_3$, $R_2 = $ ——$(CH_2)_n Cl$; $n = 1$-$4$;
Approach B:
$R_1 = H$, $R_2 = $ ——$(CH_2)_n Cl$; $n = 1, 2, 5, 6$;
Approach C:
$R_1 = H$, $R_2 = $ ——$NH(CH_2)_n COOH$; $n = 5$-$9$;

PI3K Binding Template
Approach A, B:
$R_3 = NH_2(CH_2)_n$——CO——; $(CH_3)NH(CH_2)_n$——CO——;
$n = 2$-$6$;
Approach C:
$R_3 = H$;

Synthetic Scheme (Approach A, B):

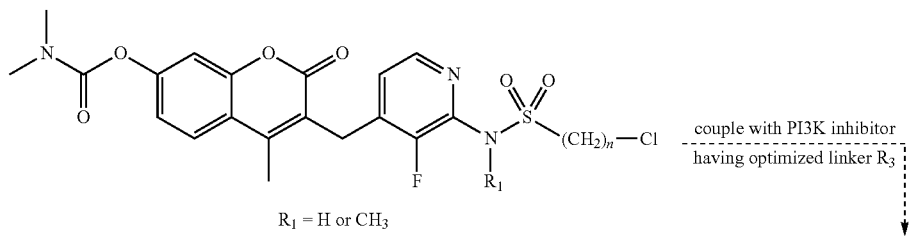

$R_1$ = H or $CH_3$ couple with PI3K inhibitor having optimized linker $R_3$

Synthetic Scheme (Approach C):

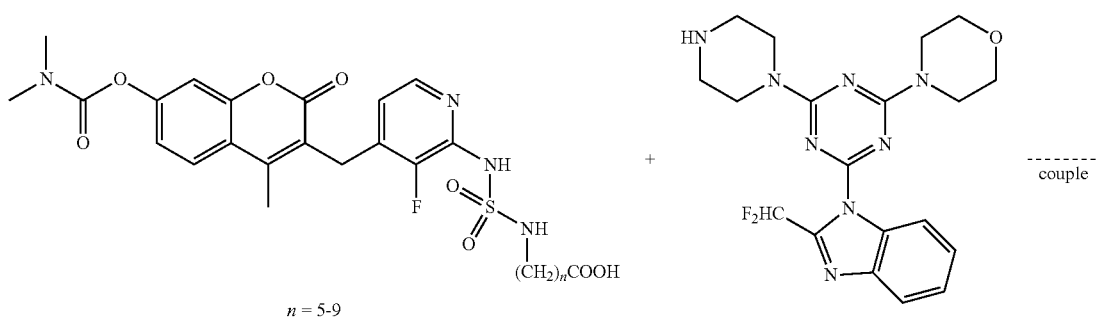

n = 5-9

Dual MEK/PI3K Inhibitors couple

The three synthetic approaches (A, B and C) of Scheme I can be used to synthesize a present dual MEK/PI3K inhibitor. Approaches A and B focus on the design of coumarin sulfonamide derivatives similar in structure to MV3-65A below. In Approach A, the analogs retain the N-methyl sulfonamide group because this analog retained both MEK and PI3K inhibition in the cellular assays. Although N-methylation at sulfonamide does lead to a 3-4 fold drop in inhibitor potency, we expect incorporation of the 6-fluoro-2-pyridyl structure in the MEK binding portion to significantly overcome the loss of affinity due to N-methylation. In Approach B, analogs with the NH sulfonamide structure with variations in the linker portion designed to disrupt cyclization by preventing the formation of stable 5- or 6-membered ring structures.

In Approach C, (ω-haloalkyl)aminosulfonamide linkers at the MEK binding motif are used, which then are directly coupled to the PI3K binding piperazine nitrogen by an amide bond. Inclusion of the aminosulfonamide group in the linker is expected to significantly improve its MEK binding affinity based on the published SAR data for these compounds. Synthesis entails converting the primary amino functionality of the pyridyl group to the corresponding N-sulfamoyl derivative by treatment with sulfuryl chloride followed by condensation with the appropriate aminoalkanoate ester derivative. Following ester deprotection, the resulting acid is coupled with the PI3K inhibitor ligand via an amide linkage using methodology similar to that described in Scheme II.

The following illustrates non-limiting methods of synthesizing a dual MEK/PI3K inhibition of structural formula (I) from a coumarin-based MEK inhibitor and a triazine-based PI3K inhibitor.

The synthetic steps for the synthesis of a dual MEK/PI3K binding ligand (MV3-65A) and the in vitro MEK and PI3K binding affinities for intermediates and a present compound are shown in following Schemes II-IV. Synthesis of the MEK and PI3K binding motifs were conducted using previously-reported methodologies, with additional structural modifications undertaken to accomplish a final linking of the two ligands. The modifications include (a) introduction of a (3-chloropropylsulfuryl) group at the 3-amino functionality of the MEK binding portion (MV3-61A) and (b) replacement of a morpholine group in the original PI3K binding ligand with a piperazine group to serve as a synthetic handle for the final coupling step (MV3-42B). Synthesis of the PI3K binding (MV3-46A) and MEK binding (MV3-63A) motifs are shown in Schemes II and III, respectively. Initial attempts to couple the MEK binding motif MV3-61A with the PI3K binding MV3-46A failed to provide the desired product in sufficient yield due to internal cyclization of the pendant (3-chloropropyl) group with the sulfonamide nitrogen in MV3-61A to provide the cyclic sulfonamide MV3-62A. To prevent formation of cyclization product, the sulfonamide NH was protected as an N-methyl group (compound MV3-63A; Scheme III). Coupling of MV3-63A with MV3-46A as shown in Scheme IV provided the desired hybrid ligand MV3-65A in 48% yield, which was subsequently converted to the hydrochloride salt.

In vitro binding data for the PI3K binding series (Scheme II) demonstrate high PI3K inhibition ($IC_{50}$=100 nM) for compound MV3-42B, wherein a morpholine was substituted with a piperazine group. Although attachment of the 6-nitrobenzoyl linker (MV3-44B) leads to a significant drop in affinity ($IC_{50}$>μM), conversion of the nitro group to an amino group (MV3-46A) leads to a 10-fold improvement in binding affinity ($IC_{50}$<100 nM). In the MEK binding series (Scheme III), presence of the 3-nitro functionality in MV3-34A leads to high MEK inhibition ($IC_{50}$=111 nM) and its conversion to an amino group (MV3-36A) leads to a >10-fold drop in affinity. However, attachment of the 3-chloropropylsufuryl linker group at the amine leads to significant improvement in affinity (MV3-61A; $IC_{50}$=29.3 nM). The MEK binding data also demonstrates that while the presence of the sulfonamide NH group leads to high MEK inhibition, its alkylation causes a 2.5-4 fold reduction in inhibition. For example, the $IC_{50}$ for MEK inhibition of the cyclic sulfonamide MV3-62A and the N-methylated analog MV3-63A were 78.2 nM and 120 nM, respectively. The final compound MV3-65A displayed MEK and PI3K binding inhibition values of 501 nM and 370 nM, respectively (Scheme IV).

Scheme II Synthesis of PI3K binding Pharmacophore (MV3-46A)

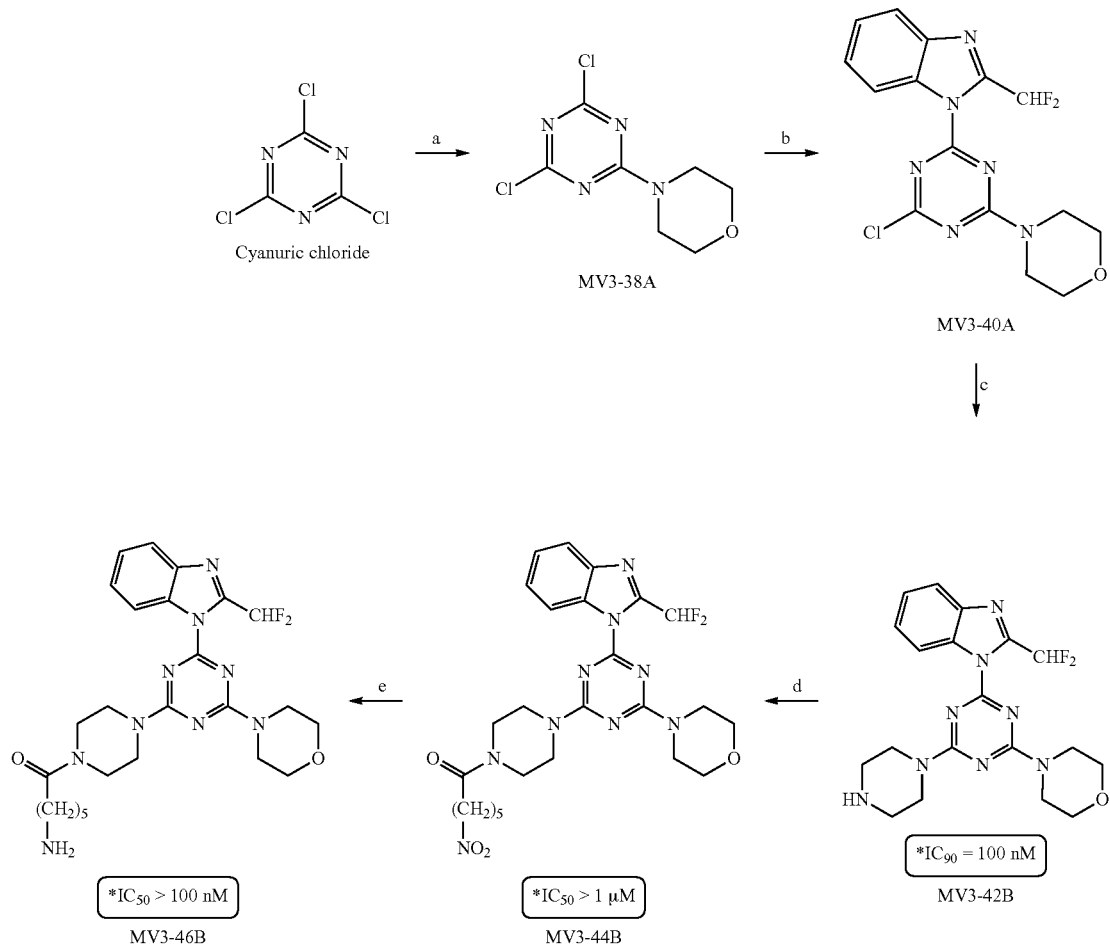

*Denotes PI3K Binding affinity
Reagents and conditions: (a) morpholine, DIPEA, DCM, -78° C.-RT, 84.7%; (b) 2-(difluoromethyl)-1H-benzimidazole, $K_2CO_3$, DMF, 85.5%; (c) piperazine, THF, reflux, 75.9%; (d) $O_2N-(CH_2)_5COCl$, $Et_3N$, $CHCl_3$, RT, 92.5%; (e) $HCOONH_4$, 10% Pd—C, $CH_3OH$, -10° C.-RT, 56.6%.

DIPEA—diisopropylethylamine
DCM—dichloromethane
$K_2CO_3$—potassium carbonate
DMF—dimethylformamide
RT—room temperature
THF—tetrahydrofuran $CHCl_3$—chloroform
$CH_3OH$—methanol
$Et_3N$—triethylamine
EtOH—ethanol
$CH_3I$—methyl iodide
$Cs_2CO_3$—caesium carbonate Scheme III Synthesis of MEK binding Pharmacophore (MV3-61A)

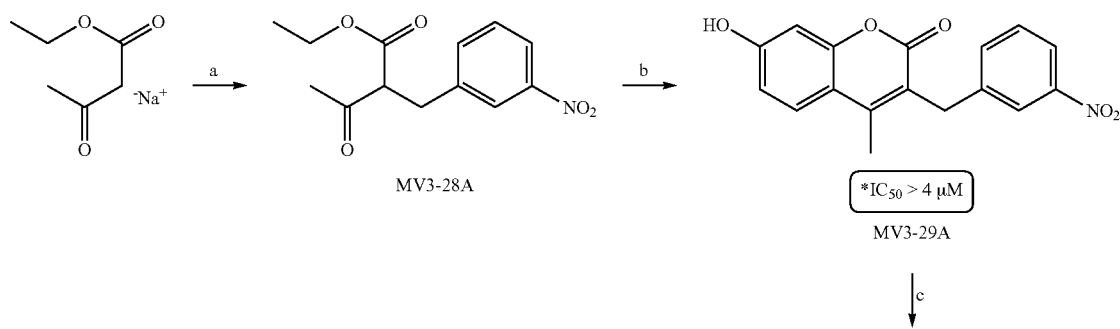

33

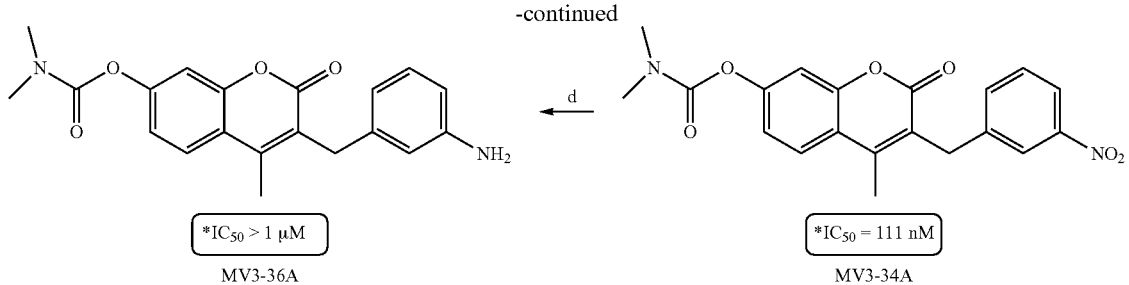

34

-continued

*IC₅₀ > 1 μM
MV3-36A

*IC₅₀ = 111 nM
MV3-34A

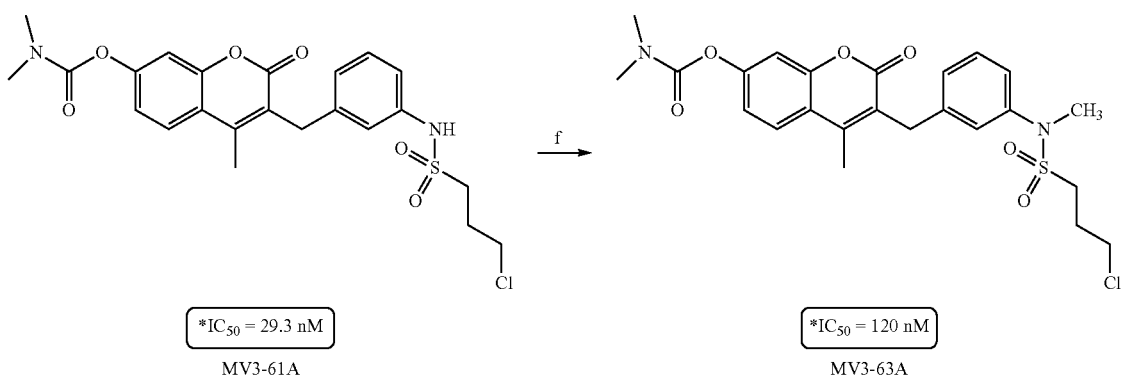

*IC₅₀ = 29.3 nM
MV3-61A

*IC₅₀ = 120 nM
MV3-63A

*Denotes MEK Binding affinity
Reagents and conditions: (a) 3-nitrobenzyl bromide, THF, 0° C.-RT, 64.5%; (b) resorcinol, conc. H₂SO₄, 0° C.-RT, 90%; (c) 1. NaH, THF, 2. (CH₃)₂NCOCl, DMAP (cat.), 93%.
(d) SnCl₂, EtOH, reflux, 90%; (e) ClSO₂(CH₂)₃Cl, Hunigs base, DMAP, DCM, 0° C.-RT, 85%; (f) CH₃I, Cs₂CO₃, DMF, 82.5%.

H₂SO₄—sulfuric acid
NaH—sodium hydride
DMAP—dimethylaminopyridine
SnCl₂—tin chloride
ETOH—ethanol Scheme IV

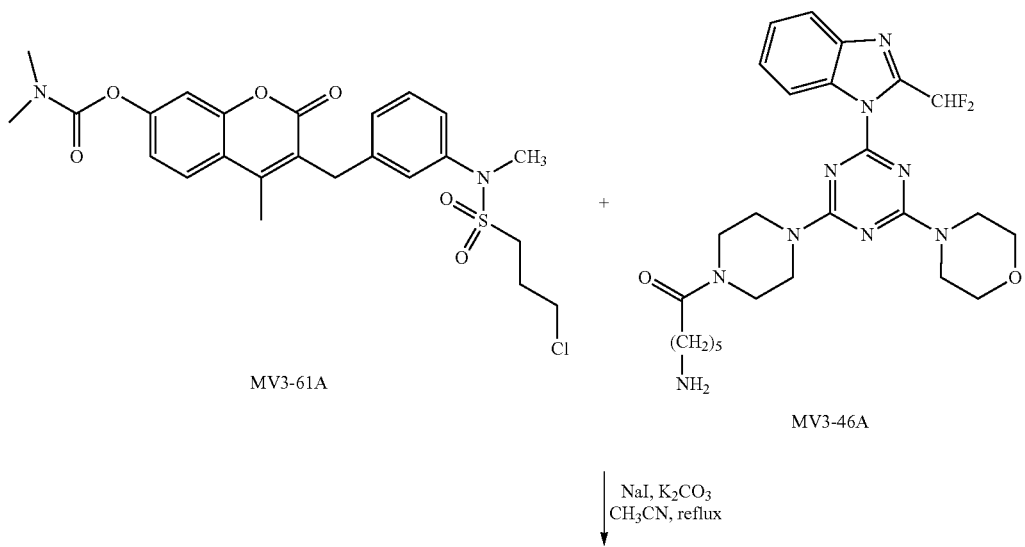

MV3-61A

MV3-46A

NaI, K₂CO₃
CH₃CN, reflux

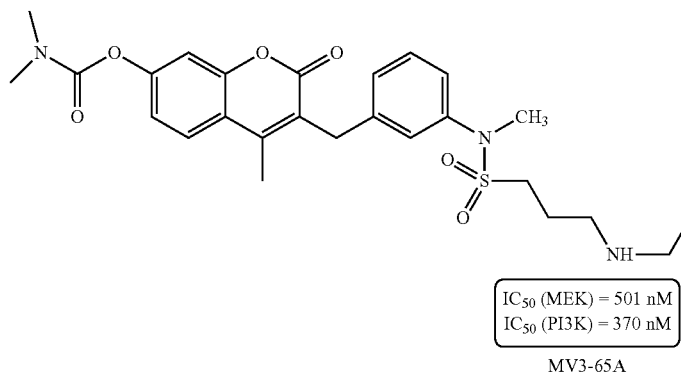

MV3-65A

IC$_{50}$ (MEK) = 501 nM
IC$_{50}$ (PI3K) = 370 nM

Data indicate that compound MV3-65A is comparably potent against all of the PI3K isoforms and lacks activity (IC$_{50}$ >10 μM) against kinases in a selectivity panel including EGFR, PKCα, ERK, and AurB. Importantly, cellular inhibition of both pERK and pAKT expression was observed.

Compound MV3-46A

A solution of the nitro analog MV3-44B (0.7 g, 1.25 mmol) in anhydrous methanol (4 mL) was treated with anhydrous ammonium formate (0.8 g, 12.7 mmol) and stirred for 10 min under a nitrogen atmosphere. The mixture was then cooled to −10° C. using an ice-salt bath, treated with 10% palladium on carbon (0.21 g) in a single portion and stirred at this temperature for an additional 1 hour. The mixture was allowed to warm to room temperature and filtered through Celite. The oil obtained following concentration in vacuo was dissolved in ethyl acetate and extracted with saturated aqueous sodium bicarbonate, brine and dried (magnesium sulfate). The crude product was flash chromatographed on silica gel with a gradient of 5%-20% methanol in dichloromethane with 1% added ammonium hydroxide to give 215 mg (32.4%) of the title compound as a cream amorphous solid. $^1$H NMR (CDCl$_3$):δ 8.32 (d, 1H, J=7.6 Hz), 7.87 (d, 1H, J=8.0 Hz), 7.55 (t, 1H, J=53.7 Hz, CHF$_2$), 7.45-7.36 (m, 2H), 3.88-3.59 (m, 16H), 3.49 (s, 2H, NH$_2$), 2.96 (t, 2H, J=7.0 Hz), 2.41-2.39 (m, 2H), 1.79-1.66 (overlapping m, 4H), 1.51-1.48 (m, 2H). HRMS (ESI+)= 530.2793; Predicted 530.2798 [M+H]$^{30}$. HPLC Retention time: 13.29 min Compound MV3-63A A solution of the ω-(3-Chloropropyl)sulfonamide analog MV3-61A (27 mg, 0.055 mmol) in anhydrous DMF (0.5 mL) was treated with CH$_3$I (27.3 mg, 12 μL, 0.19 mmol) followed by Cs$_2$CO$_3$ (36 mg, 0.11 mmol) and stirred at RT for 12 hours. The mixture was diluted with ethyl acetate, washed successively with brine, 5% aqueous sodium carbonate, water, and dried (sodium sulfate). The crude product was flash chromatographed on silica gel with a gradient of 50%-70% EtOAc in hexanes to give 23 mg (82.5%) of the title compound as a colorless viscous oil. $^1$H NMR (CDCl$_3$):δ 7.61 (dd, 1H, J=1.1, 8.0 Hz), 7.33-7.19 (m, 4H), 7.12-7.09 (m, 2H), 4.06 (s, 2H, benzylic CH$_2$), 3.62 (t, 2H, J=6.2 Hz), 3.33 (s, 3H), 3.15 (t, 2H, J=7.4 Hz), 3.13 (s, 3H), 3.03 (s, 3H), 2.48 (s, 3H), 2.27-2.23 (m, 2H).). HRMS (ESI+)=524.1614; Predicted 524.1617 [M+NH$_4$]$^{30}$ Compound MV3-65A A mixture of the sulfamoyl chloride MV3-63A (16 mg, 0.032 mmol), MV3-46A (34 mg, 0.064 mmol), anhydrous K$_2$CO$_3$ (10 mg, 0.070 mmol) and sodium iodide (5.3 mg, 0.035 mmol) in anhydrous acetonitrile (0.8 mL) was stirred at reflux under a nitrogen atmosphere for 12 h. The mixture was dissolved in ethyl acetate (25 mL) extracted with brine (25 mL) and dried (sodium sulfate). The crude product was purified by flash chromatography on silica gel with a gradient of 5%-15% methanol in dichloromethane with 1% added ammonium hydroxide to give 16 mg (50%) of the title compound as a pale yellow viscous oil. A solution of the free base in anhydrous ethanol was converted to the hydrochloride salt by treatment with one equivalent of hydrochloric acid in anhydrous diethyl ether and concentration to dryness under a nitrogen flow. $^1$H NMR (CDCl$_3$):δ 8.33 (d, 1H, J=7.6 Hz), 7.89 (d, 1H, J=7.2 Hz), 7.62 (d, 1H, J=9.4 Hz), 7.55 (t, 1H, J=53.5 Hz, CHF$_2$), 7.45-7.40 (m, 3H), 7.26-7.24 (m, 2H), 7.14-7.08 (m, 3H), 4.04 (s, 2H, benzylic CH$_2$), 3.89-3.80 (br m, 13H), 3.70 (br m, 2H), 3.59 (br m, 2H), 3.34 (s, 3H), 3.25 (t, 2H, J=7.3 Hz), 3.12 (s, 3H), 3.02 (s, 3H), 3.00 (m, 1H), 2.91 (m, 2H), 2.49 (s, 3H), 2.42 (t, 2H, J=6.6 Hz), 2.25 (m, 2H), 1.81 (m, 2H), 1.68 (m, 2H), 1.47 (m, 2H). HRMS (ESI+)=1022.4114; Predicted 1022.4129 [M+Na]$^+$. HPLC Retention time: 17.89 min.

HPLC Analysis Conditions:

Column: Waters Sunfire C18; 5μ, (250×4.6) mm

Mobile Phase:

A: Deionized water containing 0.1% trifluoroacetic acid

B: Acetonitrile containing 0.1% trifluoroacetic acid

Solvent Elution: Solvent gradient increased from 10% B to 90% B over 25 min at a flow rate of 1 ml/min with UV absorbance monitoring at 254 and 280 nm.

Additional embodiments of the MEK binding pharmacore for the dual MEK/PI3K inhibitor are illustrated in Scheme IV.

Scheme V SAR of MEK binding Pharmacophore

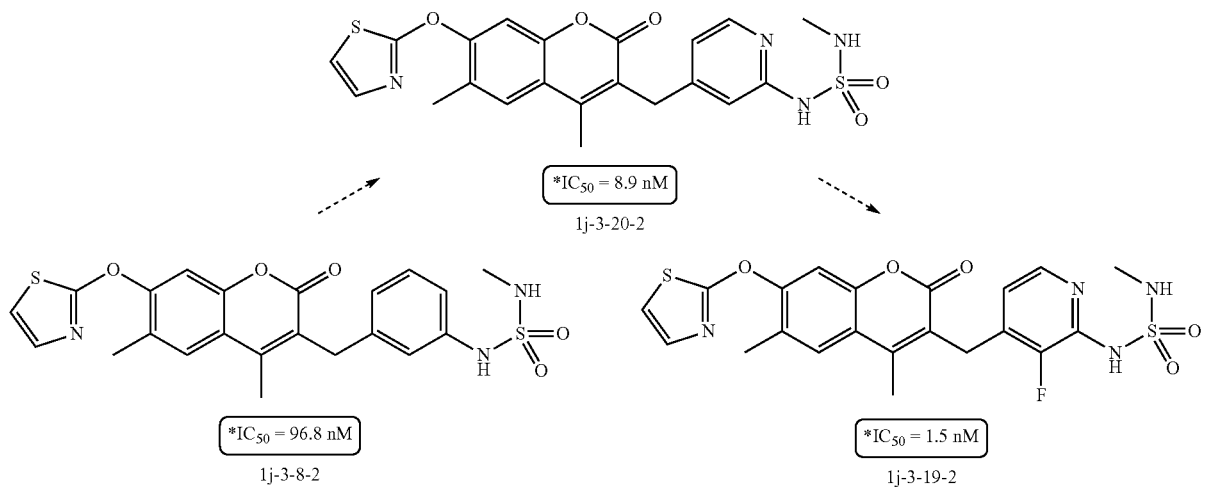

*Denotes MEK Binding affinity

In Scheme V, replacement of the phenyl ring with a 2-pyridyl ring enhances MEK inhibition by 10-fold and the additional introduction of a fluorine atom ortho to the sulfonamide results in a further 6-fold improvement in inhibition. Furthermore, the N,N-dimethylcarbamate ester group at the 7 position of the benzopyran ring provides optimum MEK inhibition among the substituents evaluated. The 6-fluoro-2-pyridyl coumarin core structure with the carbamate ester group substituent as a MEK binding template is the subject of further investigation.

Synthesis of the 6-fluoro-2-pyridyl coumarin intermediate was conducted as shown in Scheme VI from commercially available 2-chloro-3-fluoro-4-(hydroxymethyl)pyridine using standard literature procedures.

The compounds of structural formula (I) cotarget MEK and PI3K which are envisioned to act synergistically against KRAS mutants and both wild-type and mutant BRAF, thereby providing a new class of anti-cancer therapies.

Additional compounds of structural formula (I) that can be used in the methods of the present invention include the following as the MEK inhibitor pharmacophore of the dual MEK/PI3K inhibitors:

Scheme VI Synthesis of Key 6-Fluoro-2-pyridyl Coumarin Intermediate

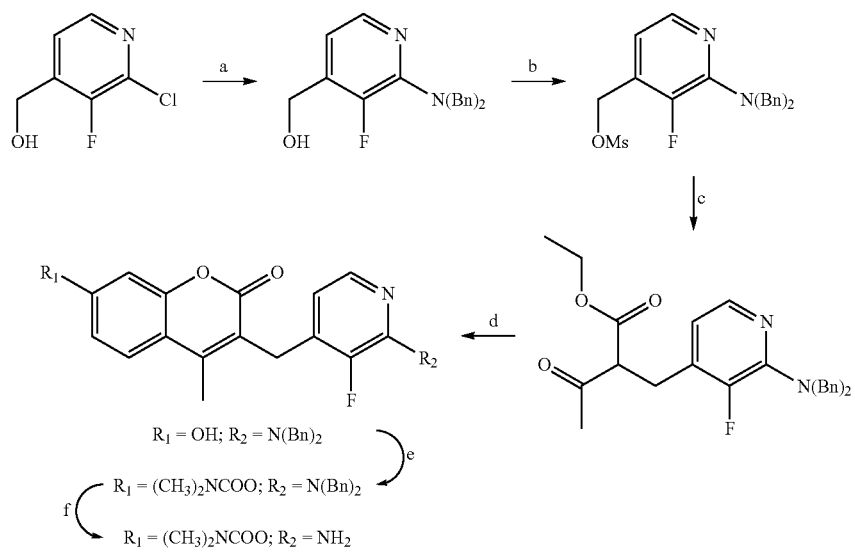

Reagents and conditions: (a) dibenzylamine, heat; (b) CH$_3$SO$_2$Cl, pyridine, DCM, 0° C.-RT; (c) ethyl acetoacetate sodium salt, THF, 0° C.-RT; (d) resorcinol, conc. H$_2$SO$_4$ 0° C.-RT; (e) (CH$_2$)$_3$NCOCl, DMAP (cat.), THF; (f) 20% Pd(OH)$_2$, HCOONH$_4$, CH$_3$OH, reflux.

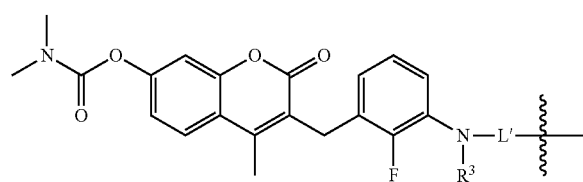
MV3-145A

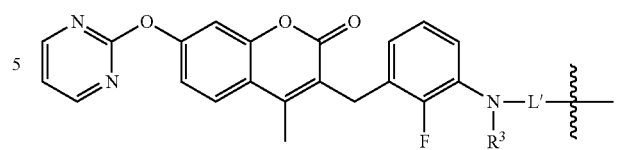
MV3-161A

In another embodiment, a present dual MEK/PI3K inhibitor has a structural formula (III), and can be used in the methods of the present invention:

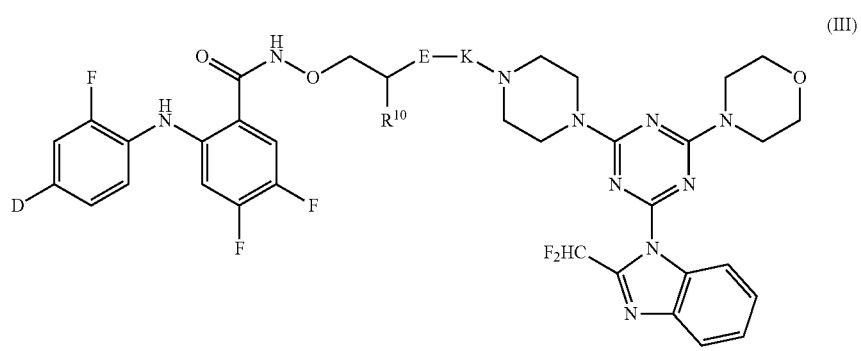
(III)

wherein D is I, HC≡C—; E is O, NH, or $NCH_3$;

K is $-(CH_2)_t-\overset{O}{\underset{\|}{C}}-$,;
t = 3-7

$-(CH_2)_r-\overset{O}{\underset{\|}{C}}-NH(CH_2)_s-\overset{O}{\underset{\|}{C}}-$, or
r = 1-3; s = 4-6

$-\overset{O}{\underset{\|}{C}}-(CH_2)_r-NH(CH_2)_s-\overset{O}{\underset{\|}{C}}-$;
r = 1-3; s = 4-6 and $R^{10}$ is H, —$CH_2OH$, or —$N(R^f)_2$, wherein $R^f$, independently, is hydrogen or $C_{1-6}$alkyl.

The synthesis of compounds of structural formula (III) is illustrated by the following synthetic Schemes (VII) and (VIII).

Scheme VII

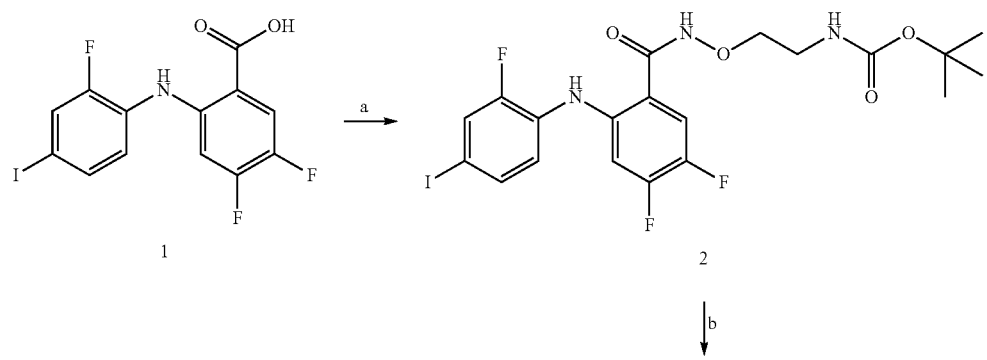

41 42
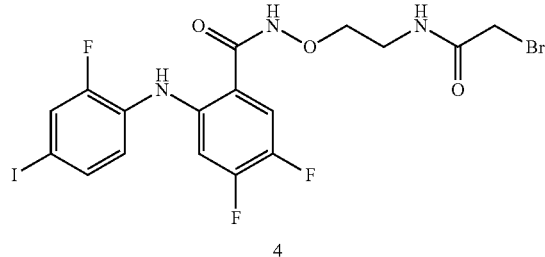
4
-continued
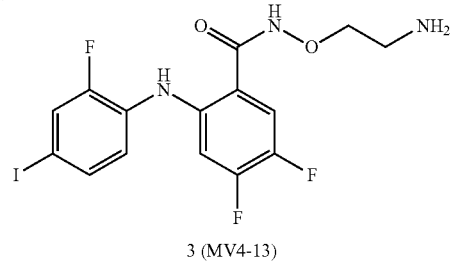
3 (MV4-13)
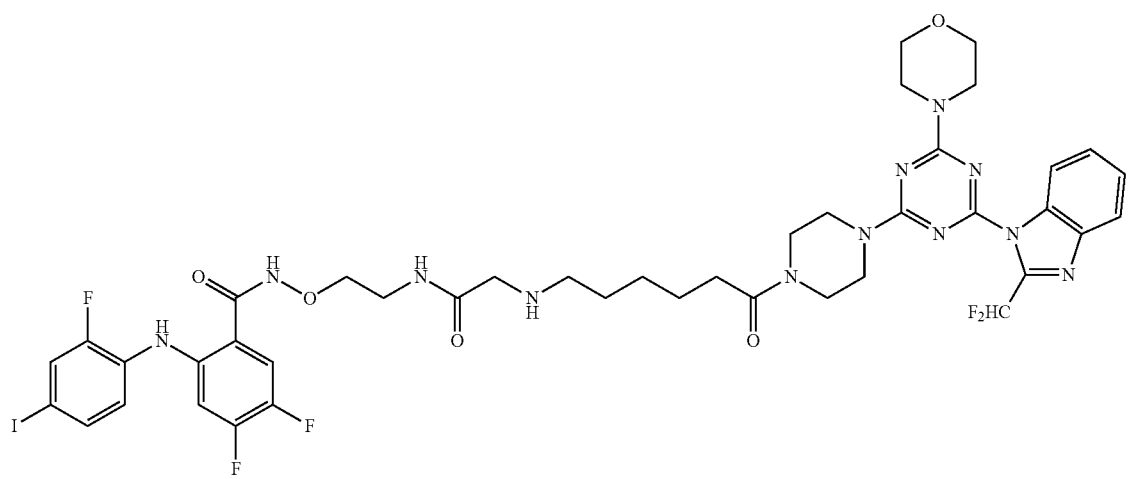
5
Reagents and conditions: (a) 1. pentafluorophenyl trifluoroacetate, pyridine, DMF, rt; 2. NH₂OCH₂CH₂NH(tBoc), DIPEA, DMF; (b) 1.0M HCl, Et₂O, rt; (c) BrCOCH₂Br, Et₃N, DCM, 0° C.; (d) compound MV3-46A, NaI, K₂CO₃, CH₃CN, reflux.
Scheme VIII
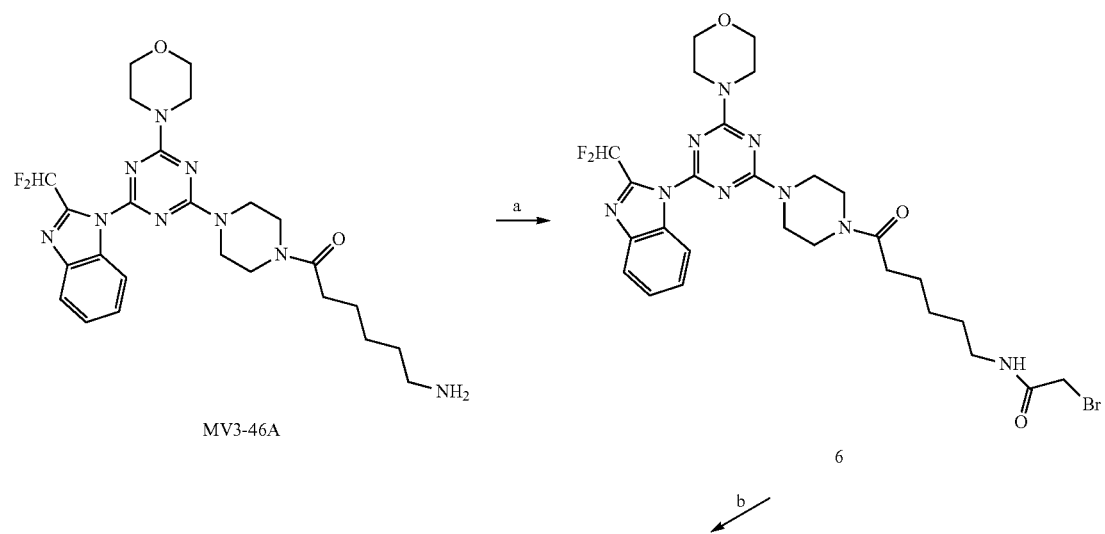

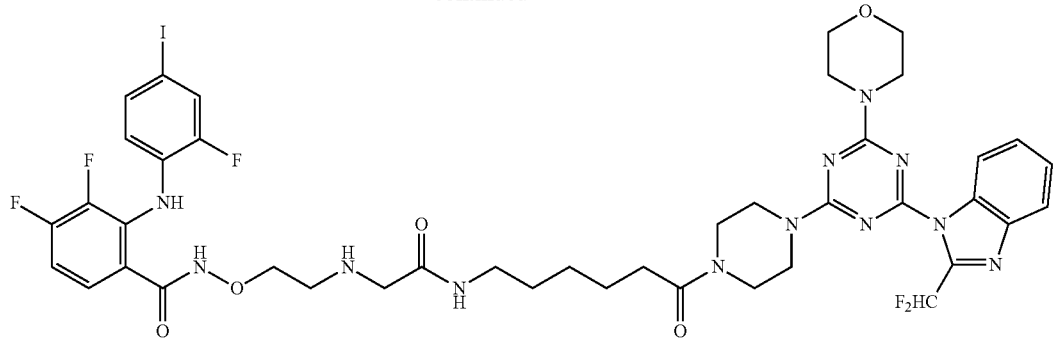

Reagents and conditions: (a) BrCOCH$_2$Br, Et$_3$N, DCM, 0° C.; (b) Compound 3, NaI, K$_2$CO$_3$, CH$_3$CN, reflux.

Additional compounds containing an MEK inhibitor pharmacophore similar to the MEK inhibitor pharmacophore of structural formula III include:

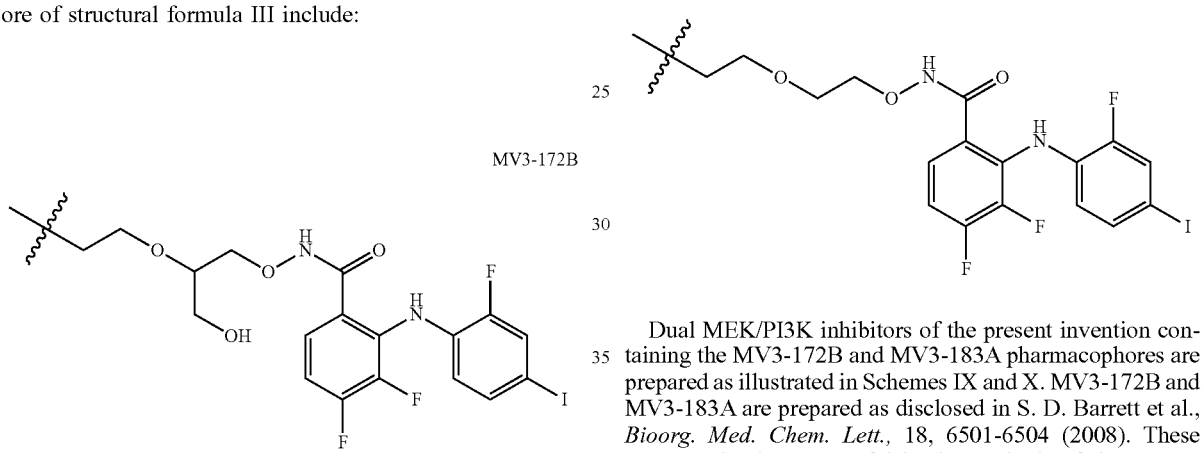

Dual MEK/PI3K inhibitors of the present invention containing the MV3-172B and MV3-183A pharmacophores are prepared as illustrated in Schemes IX and X. MV3-172B and MV3-183A are prepared as disclosed in S. D. Barrett et al., *Bioorg. Med. Chem. Lett.*, 18, 6501-6504 (2008). These compounds also are useful in the methods of the present invention.

Scheme IX

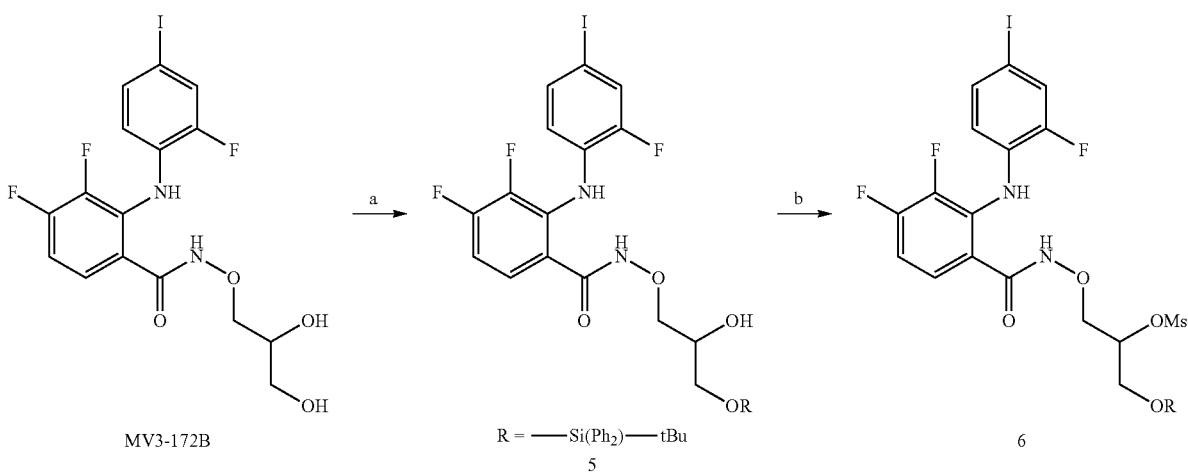

-continued
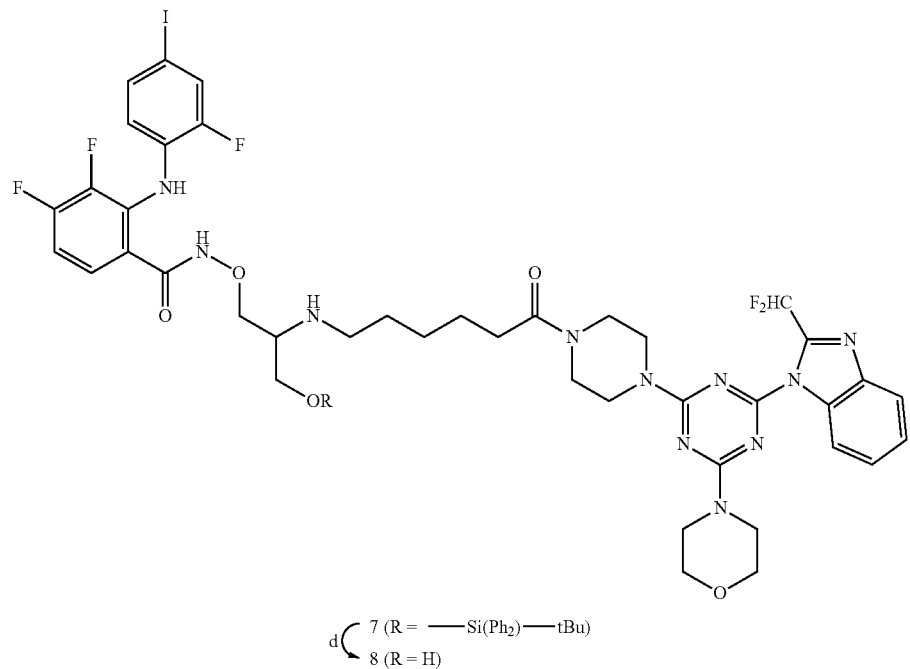
d ⎛ 7 (R = —Si(Ph₂)—tBu)
  ⎝ 8 (R = H)
Reagents and conditions: (a) t-Bu—Si(Ph₂)Cl, Et₃N, DMAP, CH₂Cl₂, rt; (b) MsCl, Et₃N, CH₂Cl₂, rt; (c) compound MV3-46A, NaI, K₂CO₃, CH₃CN, reflux; (d) TBAF, CH₂Cl₂, rt.
Scheme X
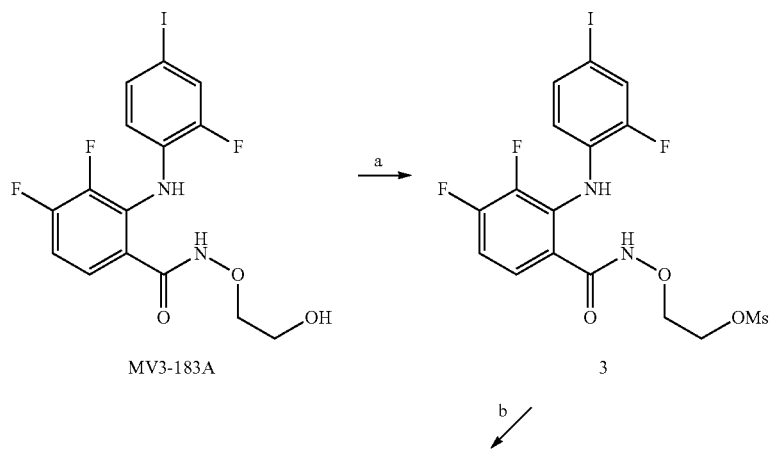

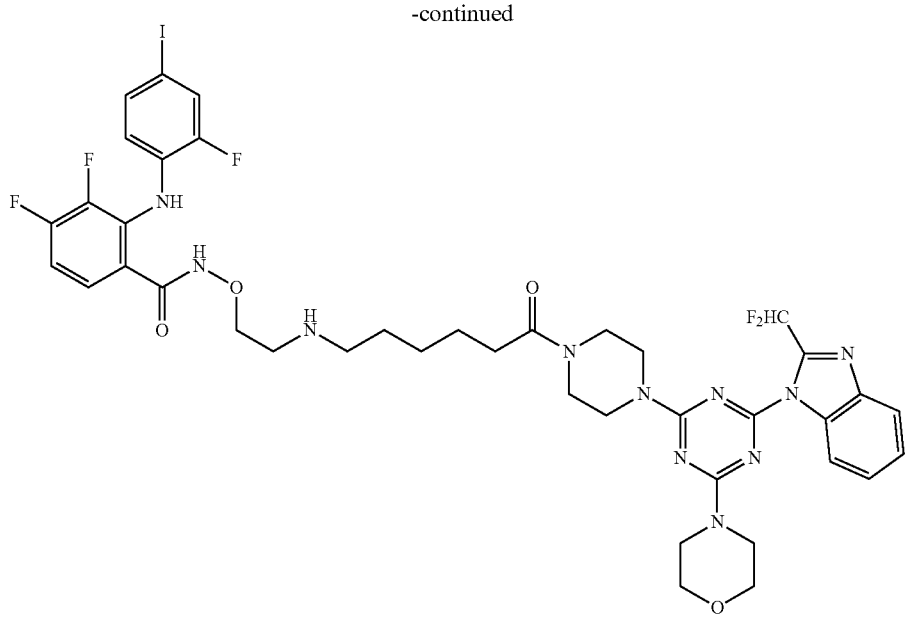

4

EXPERIMENTALS

Quantitation of PI3K lipid kinase activity of a present compound is determined with purified enzyme using the fluorescence-based Adapta™ TR-FRET assay from InVitrogen (Wisconsin, USA). Quantitation of MEK1 kinase activity of a present compound is determined with purified enzyme using the LanthaScreen® displacement binding assay (Tracer 236) from InVitrogen (Wisconsin, USA). Cellular screening is carried in cultured Panc-1 cells treated for 1 hour with varied doses of the test compound. Effects on pERK and pAKT expression are evaluated by immunoblotting using phospho-specific antibodies (pAKT [Ser473] and pERK1/2 [Thr202/Tyr204]) from Cell Signaling Technology.

Biological Data

MEK1 Cloning, Expression and Purification. Human cDNA encoding the crystallizable construct for human MEK1 (residues 35-393) was obtained from GeneArt and modified via PCR. The constructs were subcloned into a ligation-independent cloning platform for high-throughput expression optimization studies (Brown, et al. 2011). The baculovirus-infected insect cells were grown, harvested and purified as previously described (Ohren et al. 2004; Fischmann et al. 2009).

In Vitro Biochemical and Cell-Based Assays. Detection of PI3K lipid kinase activity was conducted with purified enzyme using the fluorescence-based Adapta™ TR-FRET assay from Invitrogen (Wisconsin, USA). Detection of the MEK1 kinase activity was conducted with purified enzyme using the LanthaScreen® displacement binding assay (Tracer 236) from Invitrogen (Wisconsin, USA). Evaluation of off-target kinase activity was conducted against the kinase screening panel provided by Invitrogen (Wisconsin, USA).

Cells were cultured in Dulbecco's Modified Eagle's Medium (DMEM) and 10% FBS, and grown in a 37° C. incubator with 5% $CO_2$. Cells were plated at $3 \times 10^5$ cells/ well in 6 well plates, and the following day were treated for 1 hr at 37° C. Cells were lysed in 50 mM Tris, 1% NP-40, 150 mM NaCl, 10% glycerol, 1 mM EDTA with with 1× protease inhibitor (complete; Roche Applied Science) and phosphatase inhibitors (PhosSTOP, Roche Applied Science). Protein concentration was determined with a Dc Protein Assay Kit (BioRad). Proteins were resolved by SDS-PAGE and transferred to nitrocellulose membranes. Primary antibodies (p-Akt (Ser473), p-ERK-1/2 (Thr202/Tyr204) from Cell Signaling Technology were allowed to bind overnight at 4° C., and used at a dilution of 1:1000 to 1:2000. After washing in TBS-Tween, membranes were incubated with horseradish peroxidase-conjugated secondary antibodies diluted 1:10,000 for 1 hour. Membranes were washed with TBS-Tween and incubated for 1 minute with enhanced chemiluminescence reagent (GE Healthcare) before exposing to film.

REFERENCES

1. A T Baines et al., *Future Med Chem.* 2011; 3(14):1787-808.
2. A Jemal et al., *CA Cancer J Clin.* 2010; 60(5):277-300.
3. J S Sebolt-Leopold et al., *Nat Rev Cancer.* 2004; 4(12):937-47.
4. E Castellano et al., *Genes Cancer.* 2011; 2(3):261-74.
5. J S Sebolt-Leopold *Clin Cancer Res.* 2008; 14(12): 3651-6.
6. C Montagut et al., *Cancer Lett.* 2009; 283(2):125-34.
7. J A McCubrey et al., *Expert Opin Emerg Drugs.* 2009; 14(4):633-48.
8. F A Karreth et al. *Mol Cell.* 2009; 36(3):477-86.
9. P I Poulikakos et al. *Nature.* 2010; 464(7287):427-30.
10. G Hatzivassiliou et al., *Nature.* 2010; 464(7287):431-5.
11. S Wee et al., *Cancer Res.* 2009; 69(10):4286-93.
12. P M Lorusso et al., *J Clin Oncol.* 2005; 23(23):5281-93.
13. J R Infante et al., *Lancet Oncol.* 2012; 13(8):773-81.
14. J A Engelman et al., *Nat Med.* 2008; 14(12):1351-6.
15. K Yu et al., *Cancer Biol Ther.* 2008; 7(2):307-15.

16. O K Mirzoeva et al., *Cancer Res.* 2009; 69(2):565-72.
17. A Carracedo et al., *J Clin Invest.* 2008; 118(9):3065-74.
18. M L Sos et al., *Proc Natl Acad Sci USA.* 2009; 106(43):18351-6.
19. T Shimizu et al., *Clin Cancer Res.* 2012; 18(8):2316-25.
20. C L Sawyers, *J Clin Oncol.* 2002; 20(17):3568-9.
21. K B Kim et al., 2013. *J Clin Oncol.* 2012; 31(4):482-9.
22. G S Falchook, et al., *Lancet Oncol.* 2012; 13(8):782-9.
23. S Bagrodia et al., *Pigment Cell Melanoma Res.* 2012; 25(6):819-31.

What is claimed:
1. A compound having a structure:

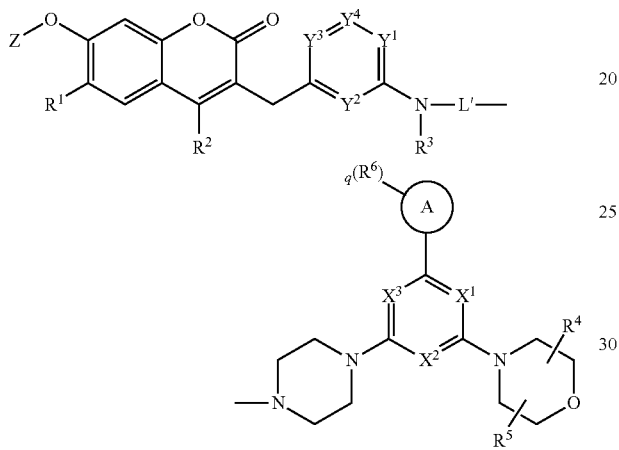

wherein Z is a heteroaryl group or $R^aR^bNCO—$;
$Y^1$ and $Y^2$, independently, are N or $CR^c$;
$Y^3$ and $Y^4$, same or different, are each $CR^d$;
$X^1$, $X^2$, and $X^3$, independently, are N or $CR^3$, wherein at least one of $X^1$, $X^2$, and $X^3$ is N;
A is cycloalkyl, heterocycyl, aryl, or heteroaryl;
L' is J-$(CH_2)_n$—K, wherein n is an integer 3, 4, 5, 6, 7, 8, or 9, J-$(CH_2)_m$—N($R^7$)—$(CH_2)_p$—K, wherein m and p, independently, are integers 0, 1, 2, 3, 4, 5, or 6, and $R^7$ is H, methyl, ethyl, propyl or butyl;
$(CH_2O)_l$, $(CH_2CH_2O)_l$, wherein l is 5,6, 7, 8, or 9, —(NHCHRC(=O)—)$_q$, wherein R, independently, is an amino acid residue, and q is an integer 3, 4, 5, 6, 7, 8, or 9;
J and K, independently, are (—C(=O)—, —C(=O)N—, —SO$_2$—, or —CH$_2$—;
$R^1$ is hydrogen, a halo, cyano, $C_{1-6}$alkyl, $C_{2-7}$alkenyl, carbamoyl, or $C_{2-7}$ alkynyl optionally substituted with a $C_{1-4}$acyl group;
$R^2$ is $C_{1-6}$alkyl optionally substituted with halo, OH, $C_{1-6}C(=O)R^a$, or $CH_2OC_{1-6}$alkyl;
$R^3$ is hydrogen or $C_{1-6}$alkyl;
$R^4$ and $R^5$, independently are hydrogen or $C_{1-6}$alkyl, or $R^4$ and $R^5$ are taken together with the carbon to which they are bound to form $C_{1-6}$alkylene, $C_{1-6}$heteroalkylene, $C_{2-6}$alkenylene, or $C_{2-6}$heteroalkenylene;
$R^6$, independently, is cyano, halo, nitro, $C_{1-6}$alkyl, halo$C_{1-6}$ alkyl, $C_{2-6}$alkenyl, $C_{2-6}$alkynyl, $C_{3-7}$cycloalkyl, $C_{6-14}$aryl, $C_{7-15}$aralkyl, heteroaryl, heterocyclyl, —C(O)$R^e$, —C(O)O$R^e$, —C(O)N($R^e$)$_2$, —C(NR$^e$)N($R^e$)$_2$, —O$R^e$, —OC(O)$R^e$, —OC(O)O$R^e$, —OC(O)N($R^e$)$_2$, —OC(=N$R^e$)N($R^e$)$_2$, —OS(O)$R^e$, —OS(O)$_2$$R^e$, —OS(O)N($R^e$)$_2$, —OS(O)$_2$N($R^e$)$_2$, —N($R^e$)$_2$, —NR$^e$C(O)O$R^e$, —NR$^e$C(O)N($R^e$)$_2$, —NR$^e$C(=NR$^e$)N($R^e$)$_2$, —NR$^e$S(O)$R^e$, —NR$^e$S(O)$_2$$R^e$, —NR$^e$S(O)N($R^e$)$_2$, —NR$^e$S(O)$_2$N($R^e$)$_2$, —SR$^e$, —S(O)$R^e$, —S(O)$_2$$R^e$, —S(O)N($R^e$)$_2$, or —S(O)$_2$(N$R^e$)$_2$, wherein q is 0, 1, 2, or 3;
$R^a$ and $R^b$, independently, are hydrogen, $C_{1-6}$alkoxy, $C_{3-8}$cycloalkyl, or a $C_{1-6}$alkyl optionally substituted with a substituent selected from the group consisting of cyano, halo, hydroxy, $C_{1-6}$alkoxy, and —N($R^f$)$_2$, or $R^a$ and $R^b$ are taken together with the nitrogen to which they are attached to form a heterocyclyl ring;
$R^c$ is hydrogen, halo, $C_{1-6}$ alkyl, $C_{1-4}$acyl, $C_{1-4}$acyloxy, or —N($R^g$)$_2$;
$R^d$ is hydrogen, halo, or $C_{1-6}$alkyl;
$R^e$, independently, is hydrogen, $C_{1-6}$alkyl, $C_{2-6}$alkenyl, $C_{2-6}$alkynyl, $C_{3-7}$cycloalkyl, $C_{6-14}$aryl, $C_{7-15}$aralkyl, heteroaryl, or heterocyclyl;
$R^f$, independently, is hydrogen or $C_{1-6}$alkyl; and
$R^g$, independently, is hydrogen or $C_{1-4}$acyl;
or a pharmaceutically acceptable salt thereof.

2. The compound of claim 1 wherein each of $X^1$, $X^2$, and $X^3$ is N.

3. The compound of claim 1 wherein the A ring is selected from the group consisting of

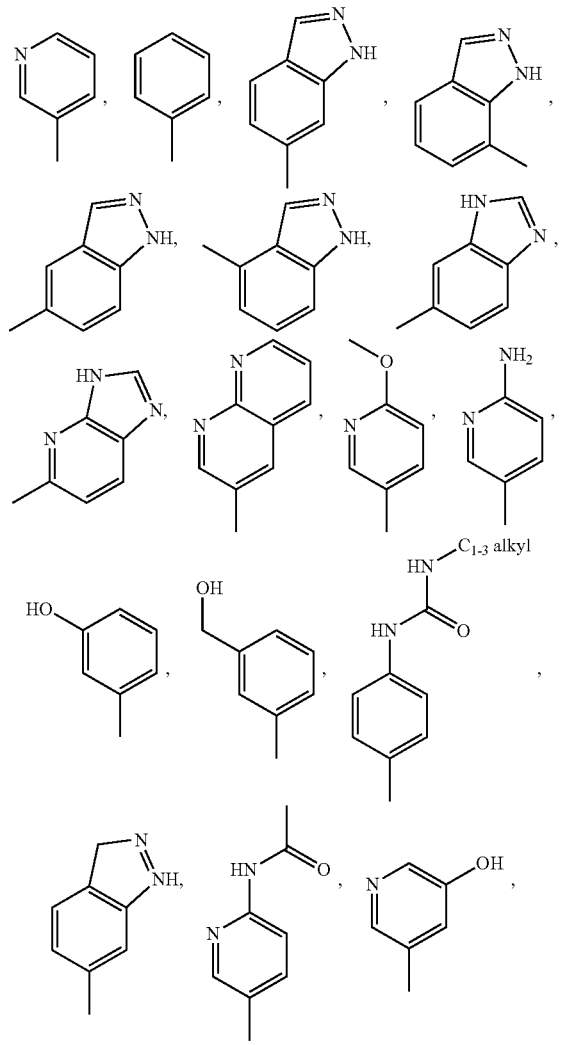

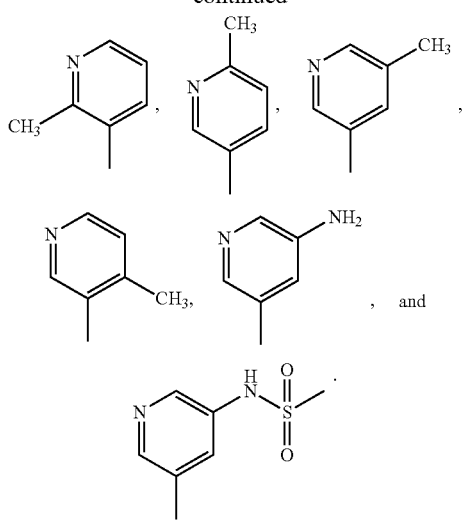

, and

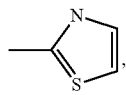

.

4. The compound of claim 1 wherein the A ring is optionally substituted with one or more of —OH, —OCH$_3$, —NH$_2$, —CH$_2$—OH, —NHC(=O)NH$_2$, —NHC(=O)NHC$_{1-3}$alkyl, —NH—C(=O)C$_{1-3}$alkyl, —NHSO$_2$C$_{1-3}$alkyl, or haloC$_{1-6}$alkyl.

5. The compound of claim 1 wherein the A ring is benzimidazolyl, optionally substituted with a haloC$_{1-6}$alkyl group.

6. The compound of claim 1 wherein L is —(CH$_2$)$_{2,3}$—NH—(CH$_2$)$_{2-5}$— or —(CH$_2$)$_{5-9}$—.

7. The compound of claim 1 wherein Z is —C(=O)NR$^a$R$^b$,

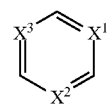

,

2-N-methylimidazolyl, 2-pyrimidinyl, 2-thiazolyl, 3-thienyl, 2-pyridinyl, 3-pyridinyl, 4-pyridinyl, 2-benzothiazolyl,

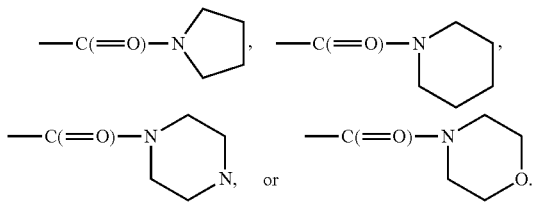

8. The compound of claim 1 wherein R$^3$ is H or C$_{1-6}$alkyl.

9. The compound of claim 1 wherein Y$^1$ and Y$^2$ each are CR$^c$ and Y$^3$ and Y$^4$ each are CR$^d$.

10. The compound of claim 1 wherein

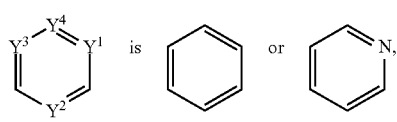

each optionally substituted with a halo group.

11. The compound of claim 1 wherein

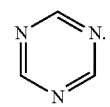

12. The compound of claim 1 wherein R$^1$ is CH$_3$, F, Cl, I, CN, or C(=O)NH$_2$.

13. The compound of claim 1 wherein R$^2$ is CH$_3$, CH$_2$CH$_3$, CH$_2$F, CH$_2$Br, CH$_2$CH$_2$OH, CH$_2$CH(CH$_3$)OH, CH$_2$C(=O)CH$_3$, CH$_2$C(=O)OCH$_3$, CH$_2$C(=O)OH, CH$_2$C(=O)NH$_2$, CH$_2$C(=O)N(CH$_3$)$_2$, or CH$_2$OCH$_3$.

14. The compound of claim 1 having a structure

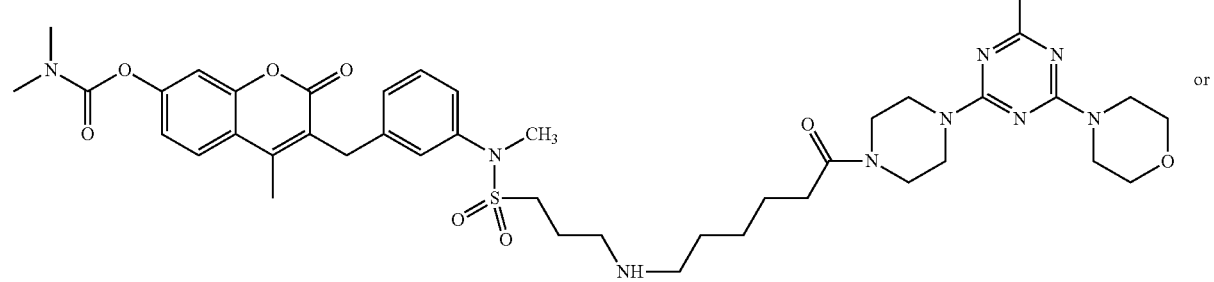

or

-continued

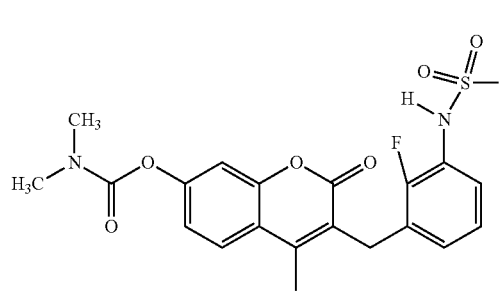 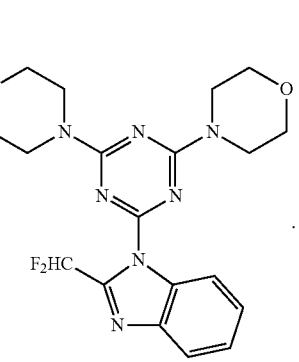

15. A pharmaceutical composition comprising a compound of claim 1 and a pharmaceutically acceptable carrier or vehicle.

16. The compound of claim 1 wherein

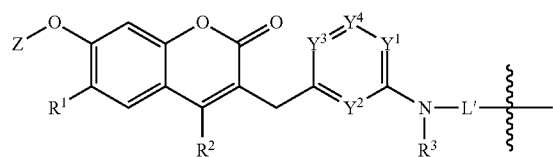

has a structure

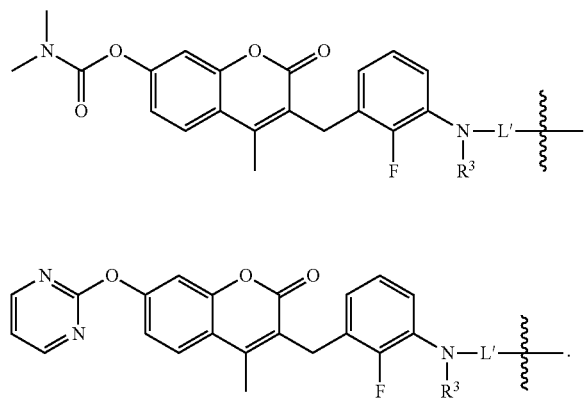

17. A compound having a structure:

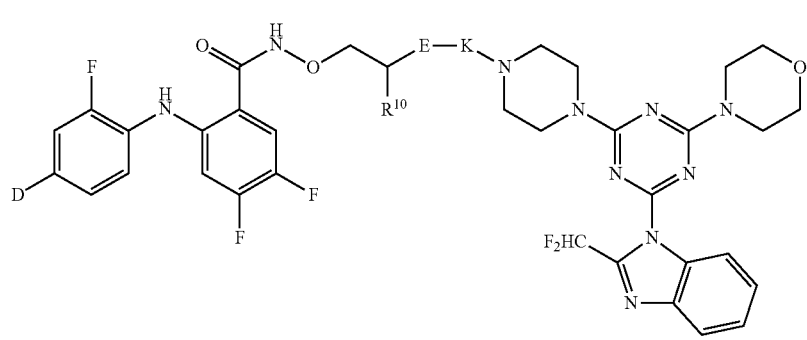

wherein D is I or HC≡C—; E is O, NH, or NCH$_3$;

K is —(CH$_2$)$_t$—C(O)—,; t = 3-7

—(CH$_2$)$_r$—C(O)—NH(CH$_2$)$_s$—C(O)—, or  r = 1-3; s = 4-6

—C(O)—(CH$_2$)$_r$—NH(CH$_2$)$_s$—C(O)—;  r = 1-3; s = 4-6 and

R$^{10}$ is H, —CH$_2$OH, or —N(R$^f$)$_2$, wherein R$^f$, independently, is hydrogen or C$_{1-6}$alkyl.

18. The compound of claim 17 wherein R$^{10}$ is H or —CH$_2$OH.

19. The compound of claim 17 wherein D is I.

20. A compound selected from the group consisting of
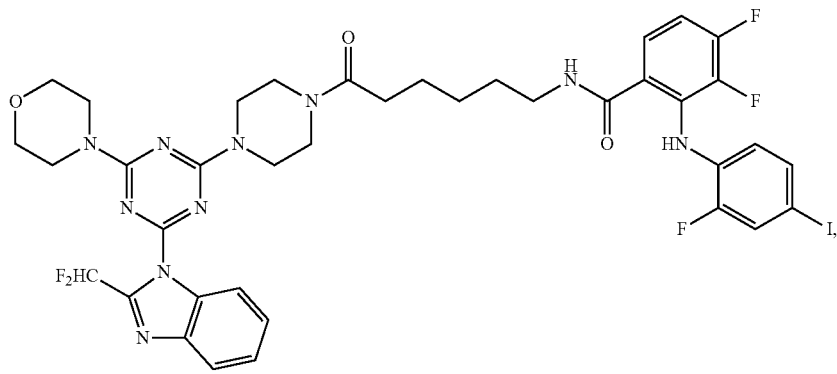
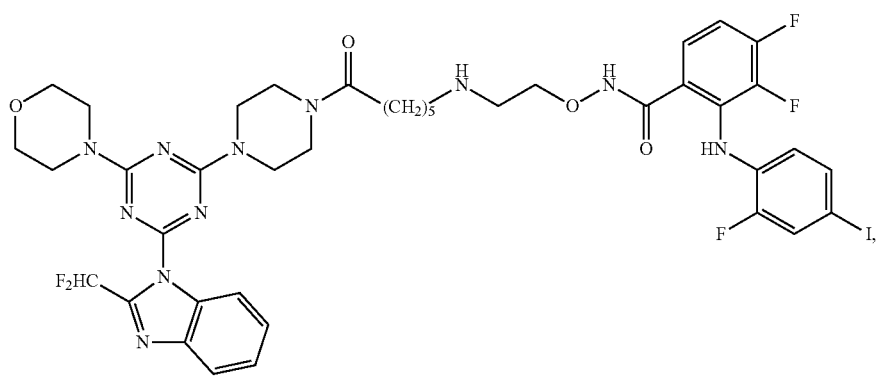
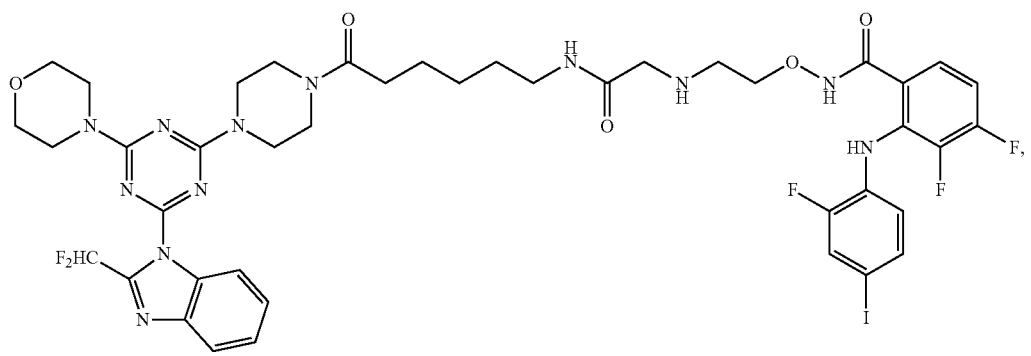
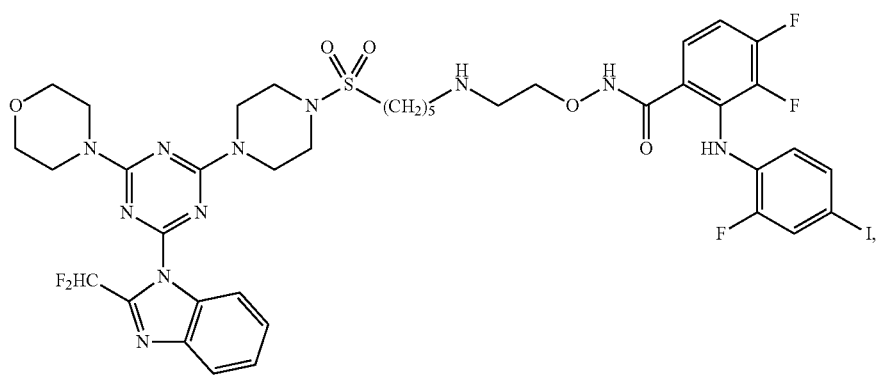

-continued
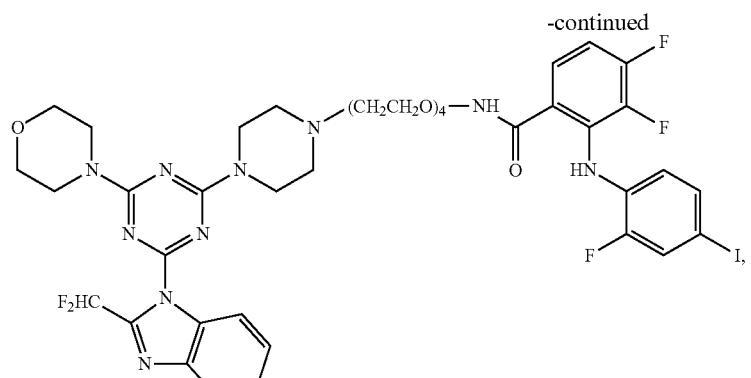
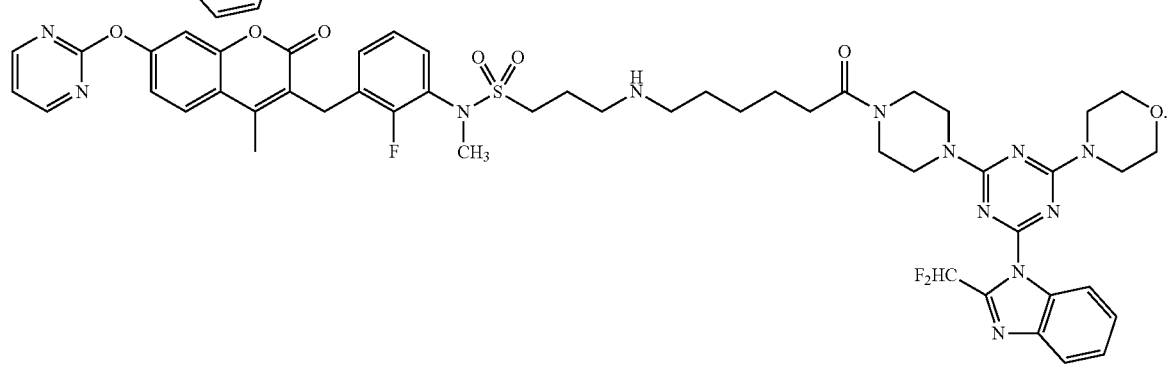
* * * * *